United States Patent
Fawzy et al.

(10) Patent No.: US 10,858,348 B2
(45) Date of Patent: Dec. 8, 2020

(54) SALT FORMS OF 4-CYANO-N-(4,4-DIMETHYLCYCLOHEX-1-EN-1-YL)-6-(2,2,6,6-TETRAMETHYLTETRAHYDRO-2H-PYRAN-4-YL)PYRIDIN-3-YL)-1H-IMIDAZOLE-2-CARBOXIMIDE

(71) Applicant: Janssen Pharmaceutica NV, Beerse (BE)

(72) Inventors: Nagy E. Fawzy, Piscataway, NJ (US); David Breslin, Telford, PA (US)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/737,273

(22) Filed: Jan. 8, 2020

(65) Prior Publication Data

US 2020/0140421 A1    May 7, 2020

Related U.S. Application Data

(62) Division of application No. 16/289,280, filed on Feb. 28, 2019, now Pat. No. 10,562,892, which is a division of application No. 15/651,829, filed on Jul. 17, 2017, now Pat. No. 10,266,522.

(60) Provisional application No. 62/363,657, filed on Jul. 18, 2016.

(51) Int. Cl.
*C07D 405/14* (2006.01)
*C07D 401/14* (2006.01)

(52) U.S. Cl.
CPC ......... *C07D 405/14* (2013.01); *C07D 401/14* (2013.01); *C07B 2200/13* (2013.01)

(58) Field of Classification Search
CPC .................................................. C07D 405/14
USPC ....................................... 546/275.1; 514/341
See application file for complete search history.

(56) References Cited

U.S. PATENT DOCUMENTS

| 6,627,646 B2 | 9/2003 | Bakale et al. |
| 8,497,376 B2 | 7/2013 | Illig et al. |
| 2014/0045789 A1 | 2/2014 | Kolodziejczyk et al. |

FOREIGN PATENT DOCUMENTS

| WO | 2009/052237 A1 | 4/2009 |
| WO | 2014151258 | * 9/2014 |

OTHER PUBLICATIONS

Bernstein, "Polymorphism in . . ." p. 115-118, 272. (Year: 2002).
CMU Pharmaceutical polymorphism, internet p. 1-3 printout Apr. 3, 2008. (Year: 2002).
Concise Encyclopedia Chemistry, NY: Walter de Gruyter, 872-873. (Year: 1993).
Davidovich et al., "Detection of polymorphism . . ." Am. Pharm. Rev. v.&(1) p. 10, 12, 14, 16, 100.. (Year: 2004).
Dean "Analytical Chem . . ." p. 10.24-10.26. (Year: 1995).
Doelker, english translation of Ann. Pharm. Fr., 60: 161-176, pp. 1-39. (Year: 2002).
Doelker, english translation of S.T.P, Pratiques, 9(5), 399-409, pp. 1-33. (Year: 1999).
Guillory, in Brittain ed., NY Marcel Dekker, 1999, pp. 183-226.
Ivanisevic etal. "Use of X-ray . . ." Pharm. Sci. Encycl. p. 1-42.. (Year: 2010).
Jain et al., "Polymorphism in Pharmacy", Indian Drugs, 23(6) 315-329. (Year: 1986).
Kirk-Othmer Encyclopedia of Chemical Technology, 8, pp. 95-147. (Year: 2002).
Muzaffar et al., "Polymorphism and Drug Availability, etc.," J of Pharm. (Lahore), 1(1), 59-66. (Year: 1979).
Otuska et al., "Effect of Polymorphic, etc.," Chem. Pharm. Bull., 47(6) 852-856. (Year: 1999).
Rodriquez-Spong, Adv. Drug Delivery Rev. 56, 2004, 241-274.
Seddon "Pseudopolymorph" Crystal Growth design v.4(6) p. 1087 (2 pages from internet) (Year: 2004).
Singhal et al., "Drug Polymorphism, etc.," Advanced Drug Delivery reviews 56, p. 335-347). (Year: 2004).
Taday et al., "Using Terahertz, etc.," J of Pharm. Sci., 92(4), 831-838. (Year: 2003).
U.S. Pharmacopia #23, National Formulary #18, 1843-1844. (Year: 1995).

* cited by examiner

*Primary Examiner* — Patricia L Morris
(74) *Attorney, Agent, or Firm* — BakerHostetler

(57) ABSTRACT

The present disclosure discusses salt forms of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide.

7 Claims, 41 Drawing Sheets

XRPD pattern of Compound A

DSC thermogram of Compound A

TGA spectrum of Compound A

DVS spectrum of Compound A showing two cycles of adsorption/desorption

Solution H-NMR spectra of Compound A (bottom) and the sulfate salt of Compound A (top)

Solution 1H-NMR spectra of Compound A (bottom) and the phosphate salt of Compound A (top)

Solution H-NMR spectra of Compound A (bottom) and the mesylate salt of Compound A (top)

Solution ¹H-NMR spectra of Compound A (bottom) and the besylate salt of Compound A (top)

Solution 1H-NMR spectra of Compound A (bottom) and the acetate solid residue of Compound A (top)

Solution 1H-NMR spectra of Compound A (bottom) and the malonate solid residue of Compound A (top)

Solution H-NMR spectra of Compound A (bottom) and the citrate solid residue of Compound A (top)

Solution 1H-NMR spectra of Compound A (bottom) and the malate solid residue of Compound A (top)

XRPD pattern for the tosylate salt of Compound A

XRPD pattern for the acetate solid residue of Compound A

XRPD pattern for the citrate solid residue of Compound A

TGA and DSC thermograms for the sulfate salt of Compound A

TGA and DSC thermograms for the phosphate salt of Compound A

FIG. 32  TGA and DSC thermograms for the tosylate salt of Compound A

TGA and DSC thermograms for the besylate salt of Compound A

TGA and DSC thermograms for the acetate solid residue of Compound A

TGA and DSC thermograms for the malonate solid residue of Compound A

TGA and DSC thermograms for the citrate solid residue of Compound A

TGA and DSC thermograms for the malate solid residue of Compound A

DVS spectrum of the phosphate salt of Compound A showing two cycles of adsorption XRPD patterns of the phosphate salt of Compound A before (top) and after DVS (bottom)

XRPD patterns of the mesylate salt of Compound A before (top) and after DVS (bottom)

SALT FORMS OF 4-CYANO-N-(4,4-DIMETHYLCYCLOHEX-1-EN-1-YL)-6-(2,2,6,6-TETRAMETHYLTETRAHYDRO-2H-PYRAN-4-YL)PYRIDIN-3-YL)-1H-IMIDAZOLE-2-CARBOXIMIDE

CROSS-REFERENCE TO RELATED APPLICATIONS

This application is a divisional of U.S. patent application Ser. No. 16/289,280, filed on Feb. 28, 2019, which is a divisional of U.S. patent application Ser. No. 15/651,829, filed on Jul. 17, 2017 (now U.S. Pat. No. 10,266,522), which claims priority to U.S. Provisional Patent Application No. 62/363,657, filed Jul. 18, 2016. The entirety of each of these applications is hereby incorporated by reference in its entirety.

TECHNICAL FIELD

The present inventions are directed to salt forms of 4-cyano-N-(2-(4,4-dimethylcyclohex-1-en-1-yl)-6-(2,2,6,6-tetramethyltetrahydro-2H-pyran-4-yl)pyridin-3-yl)-1H-imidazole-2-carboxamide.

BACKGROUND

Protein kinases are enzymes that serve as key components of signal transduction pathways by catalyzing the transfer of the terminal phosphate from adenosine 5'-triphosphate (ATP) to the hydroxy group of tyrosine, serine and threonine residues of proteins. As a consequence, protein kinase inhibitors and substrates are valuable tools for assessing the physiological consequences of protein kinase activation. The overexpression or inappropriate expression of normal or mutant protein kinases in mammals has been demonstrated to play significant roles in the development of many diseases, including cancer and diabetes.

Protein kinases can be divided into two classes: those which preferentially phosphorylate tyrosine residues (protein tyrosine kinases) and those which preferentially phosphorylate serine and/or threonine residues (protein serine/threonine kinases). Protein tyrosine kinases perform diverse functions ranging from stimulation of cell growth and differentiation to arrest of cell proliferation. They can be classified as either receptor protein tyrosine kinases or intracellular protein tyrosine kinases. The receptor protein tyrosine kinases, which possess an extracellular ligand binding domain and an intracellular catalytic domain with intrinsic tyrosine kinase activity, are distributed among 20 subfamilies.

Feline McDonough Sarcoma (FMS) is the receptor-tyrosine kinase responsible for cellular response to colony stimulating factor-1 (CSF-1). CSF-1 is the primary growth factor for the macrophage/osteoclast lineage. Inhibitors of FMS kinase reduce macrophage survival in tissues and osteoclastogenesis in bone. Accordingly, diabetes, angiogenesis, psoriasis, restenosis, ocular diseases, schizophrenia, rheumatoid arthritis, cardiovascular disease and cancer are exemplary of pathogenic conditions that have been linked with abnormal protein tyrosine kinase activity.

4-Cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide exhibits an inhibitory activity against FMS to treat diseases where macrophages and osteoclasts are pathogenic, namely rheumatoid arthritis and cancer metastasis to bone.

There remains a need to provide alternate forms of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide.

SUMMARY

The present disclosure provides salt forms of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide. Pharmaceutical compositions comprising these salt forms and methods of using these salt forms for inhibiting colony-stimulating factor-1 receptor are also described.

BRIEF DESCRIPTION OF THE DRAWINGS

The summary, as well as the following detailed description, is further understood when read in conjunction with the appended drawings. For the purpose of illustrating the invention, there are shown in the drawings exemplary embodiments of the invention; however, the invention is not limited to the specific methods, compositions, and devices disclosed. In addition, the drawings are not necessarily drawn to scale. In the drawings.

DETAILED DESCRIPTION OF ILLUSTRATIVE EMBODIMENTS

Figure 1:
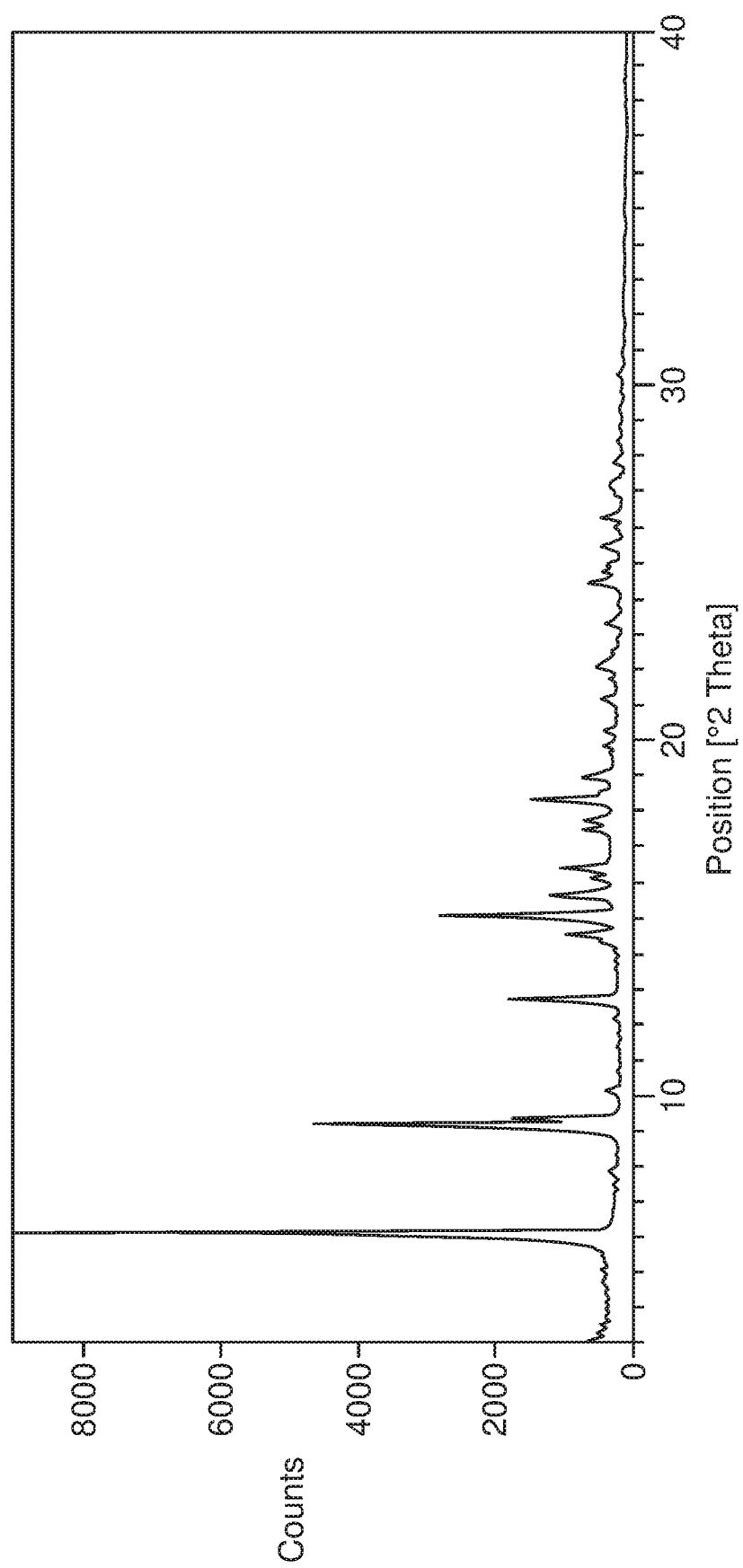
FIG. 1 is an X-ray powder diffraction (XRPD) pattern for Compound A.

The disclosure may be more fully appreciated by reference to the following description, including the following glossary of terms and the concluding examples. It is to be appreciated that certain features of the disclosed compositions and methods which are, for clarity, described herein in the context of separate aspects, may also be provided in combination in a single aspect. Conversely, various features of the disclosed compositions and methods that are, for brevity, described in the context of a single aspect, may also be provided separately or in any subcombination.

The term "subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

Some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable vehicle" refers to a diluent, adjuvant, excipient or carrier with which a compound of the disclosure is administered. A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

Further, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

Described herein are novel salt forms of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide, which has the following structure and is identified herein as "Compound A." In some embodiments, Compound A is a free base.

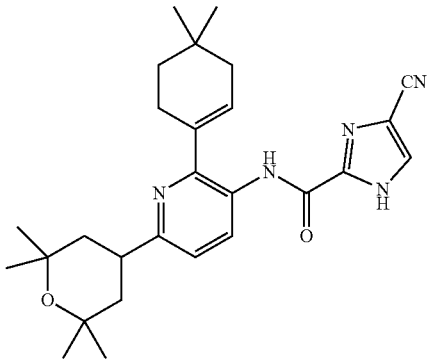

Compound A

In the development of pharmaceuticals, in particular, orally delivered drugs, it is often advantageous to have novel salt forms of such drugs that possess improved physical properties, for example, increased aqueous solubility and stability. The salt forms of Compound A described herein possess improved properties over those solid forms of Compound A previously described. In some embodiments, the salt forms have improved moisture uptake as compared to Compound A.

Compound A (as a free base) and its hydrochloride salt may be prepared, for example, as described in U.S. Pat. No. 8,497,376 and US Patent Publication No. 2014/0045789, which are incorporated herein by reference, as well as using the procedures described in Example 1. In some embodiments, Compound A is prepared from its hydrochloride salt. In other embodiments, Compound A is prepared from its hydrochloride salt as described in Example 1.

Various salt forms of Compound A are described and characterized herein. The salt forms of Compound A described herein include a sulfate salt, phosphate salt, mesylate salt, tosylate salt and besylate salt. The solid residues isolated from screening experiments using acetic acid (acetate), citric acid (citrate), malonic acid (malonate) and malic acid (malate) exhibit characteristic that suggest a form other than that of the starting material (Compound A freebase) was prepared, although the exact nature and identity of these residues was not fully determined.

Figure 11:
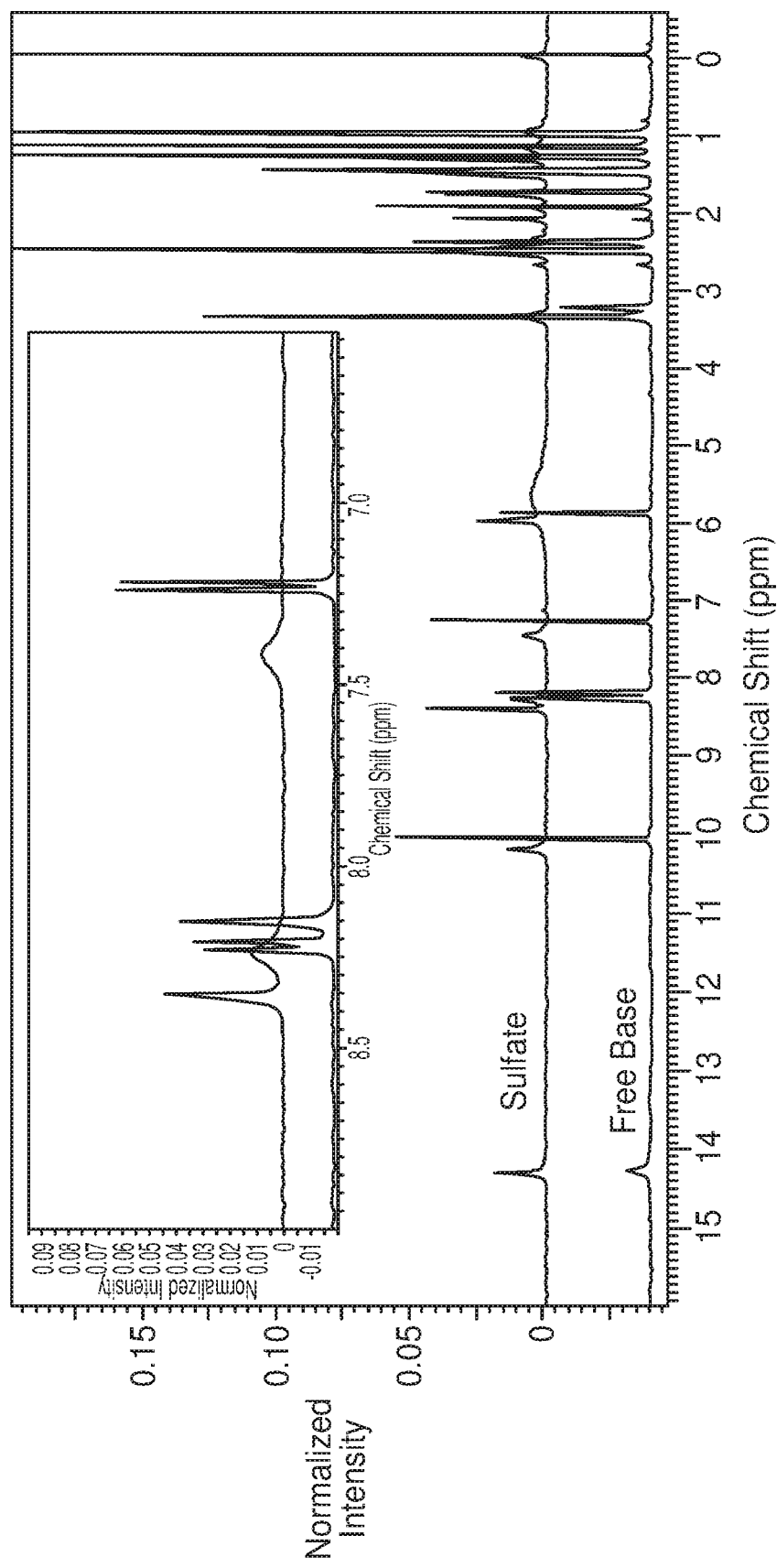
FIGS. 11-19 are solution $^1$H-NMR spectra of Compound A (bottom spectra of each of FIGS. 11-19) and the sulfate salt, phosphate salt, mesylate salt, tosylate salt, besylate salt, acetate solid residue, malonate solid residue, citrate solid residue, and malate solid residue, respectively, of Compound A (top spectra of each Figure, respectively). The shaded inserts correlated to portions of each spectrum.
Figure 20:
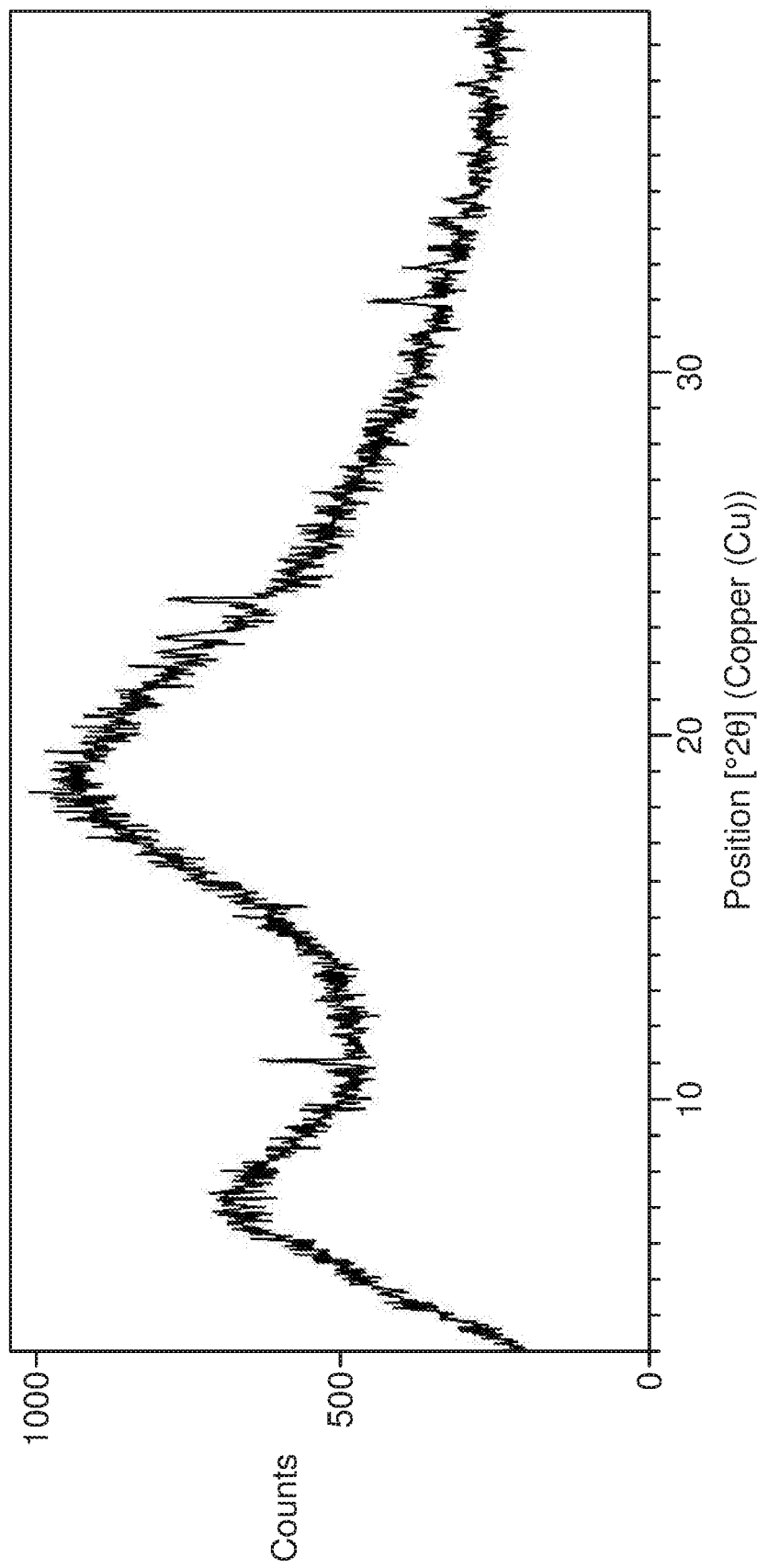
FIGS. 20-28 are XRPD patterns for the sulfate salt, phosphate salt, mesylate salt, tosylate salt, besylate salt, acetate solid residue, malonate solid residue, citrate solid residue, and malate solid residue, respectively, of Compound A.
Figure 29:
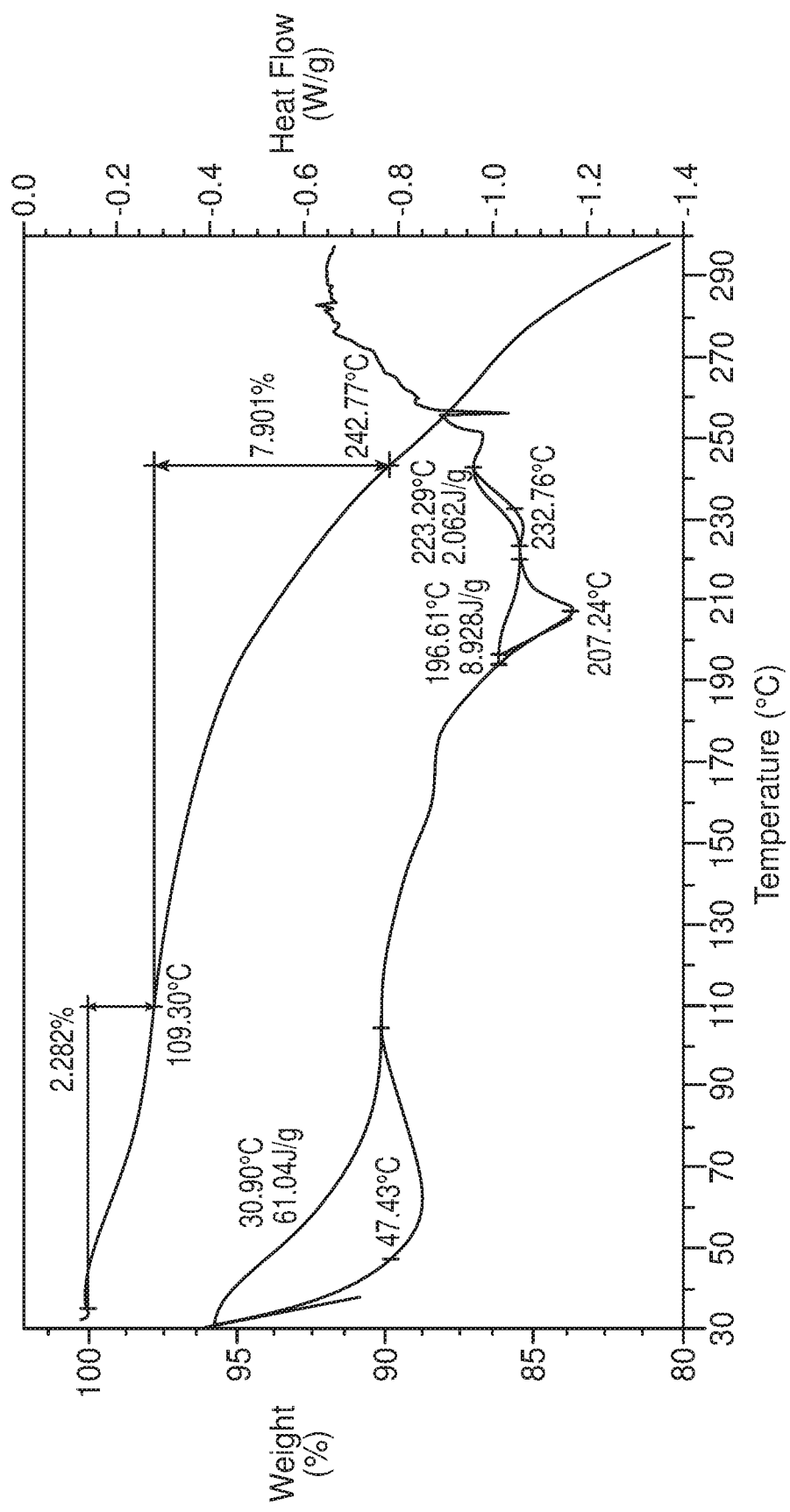
FIGS. 29-37 are TGA thermograms (starting at top) and differential scanning calorimetry (DSC) thermograms (starting at bottom) for the sulfate salt, phosphate salt, mesylate salt, tosylate salt, besylate salt, acetate solid residue, malonate solid residue, citrate solid residue, and malate solid residue, respectively, of Compound A.

In some embodiments, a sulfate salt of Compound A is provided. In one aspect, the sulfate form of Compound A is amorphous. The sulfate salt of Compound A produces a DSC thermogram comprising endothermic events with peak temperatures at about 47.4° C., about 207.2° C., and about 232.8° C. The sulfate salt of Compound A may further be characterized by a DSC thermogram of FIG. 29. The sulfate salt of Compound A may further be characterized by an $^1$H-NMR spectrum substantially as depicted in FIG. 11. The amorphous form of the sulfate salt of Compound A may be characterized by an XRPD pattern substantially as depicted in FIG. 20.

Figure 12:
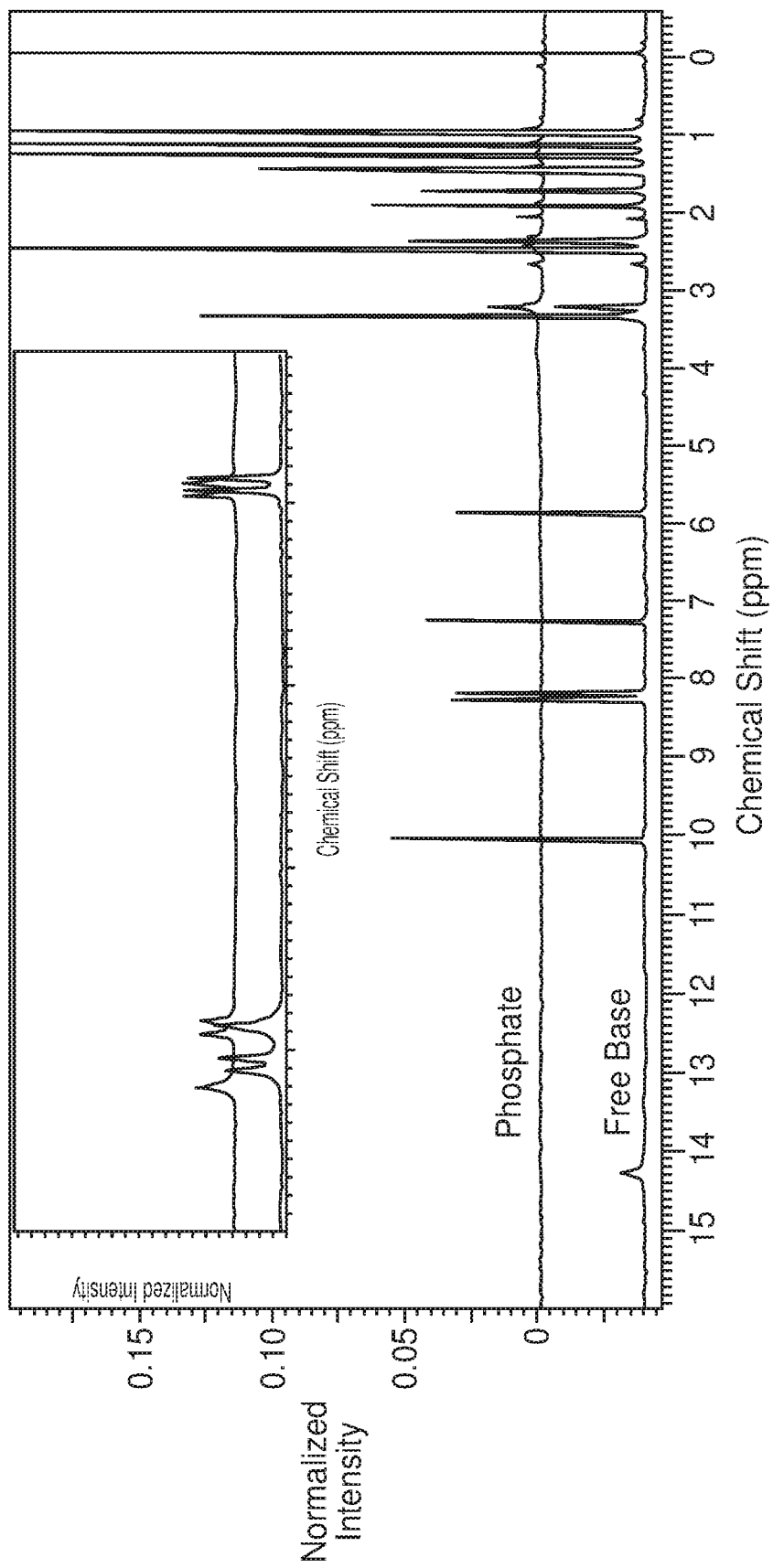
Figure 21:
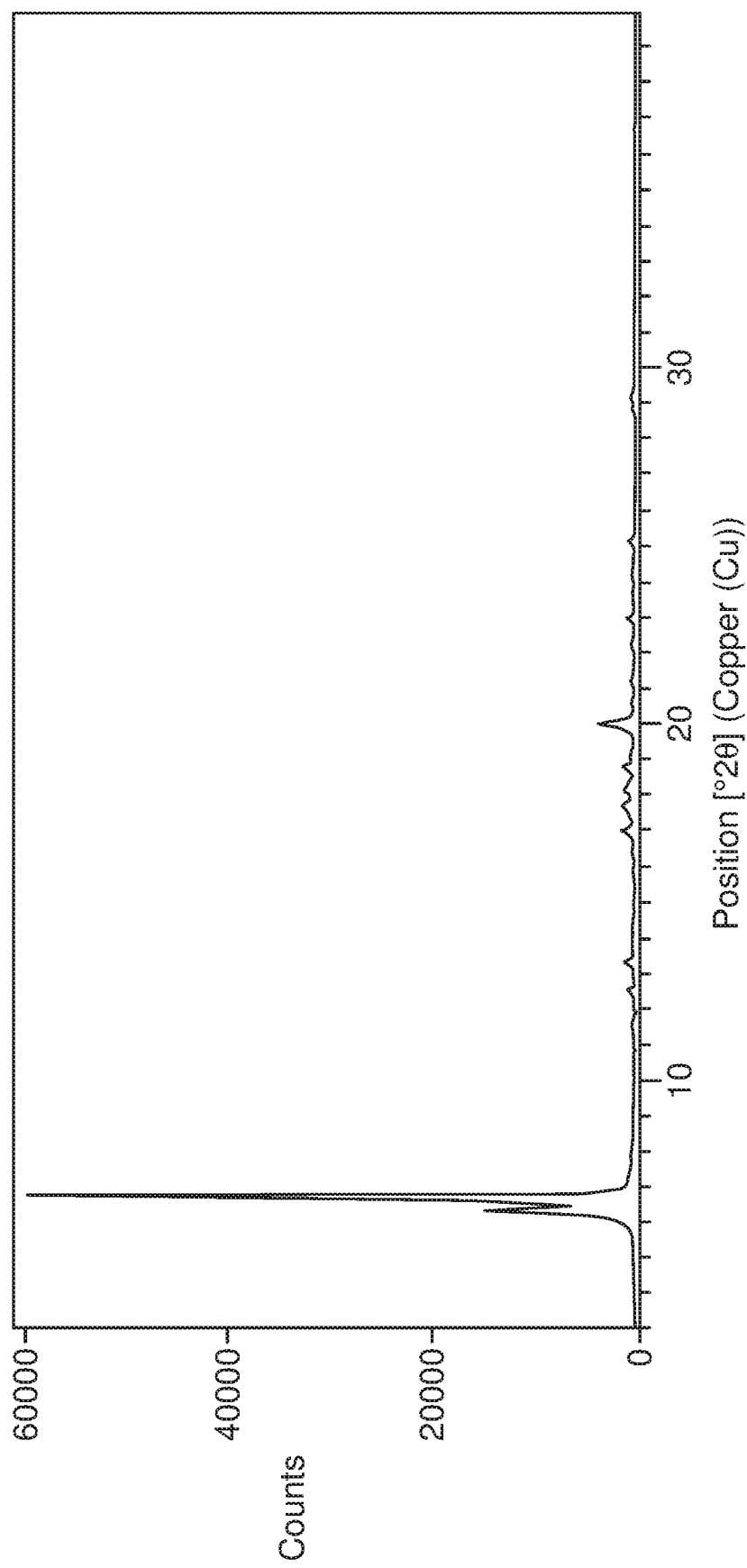
Figure 30:
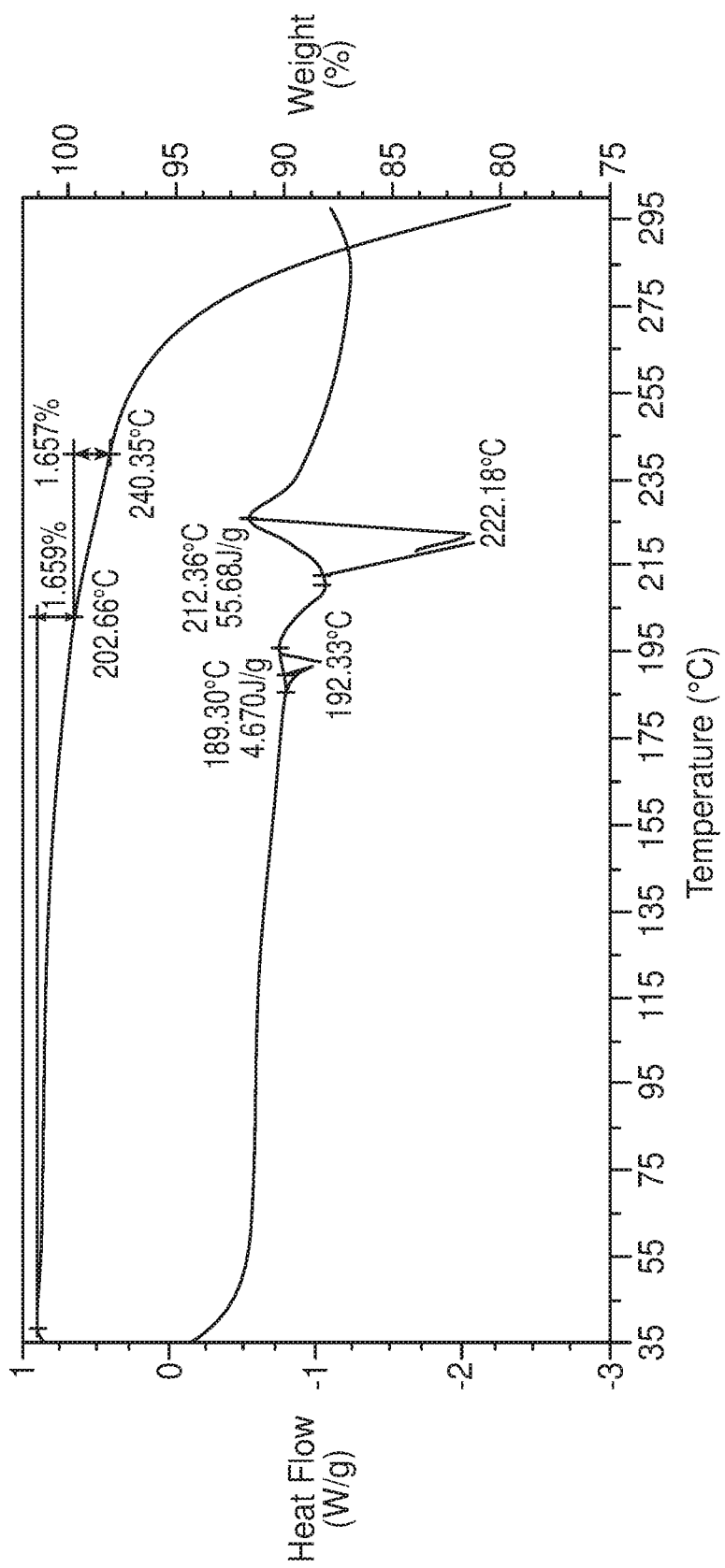
Figure 38:
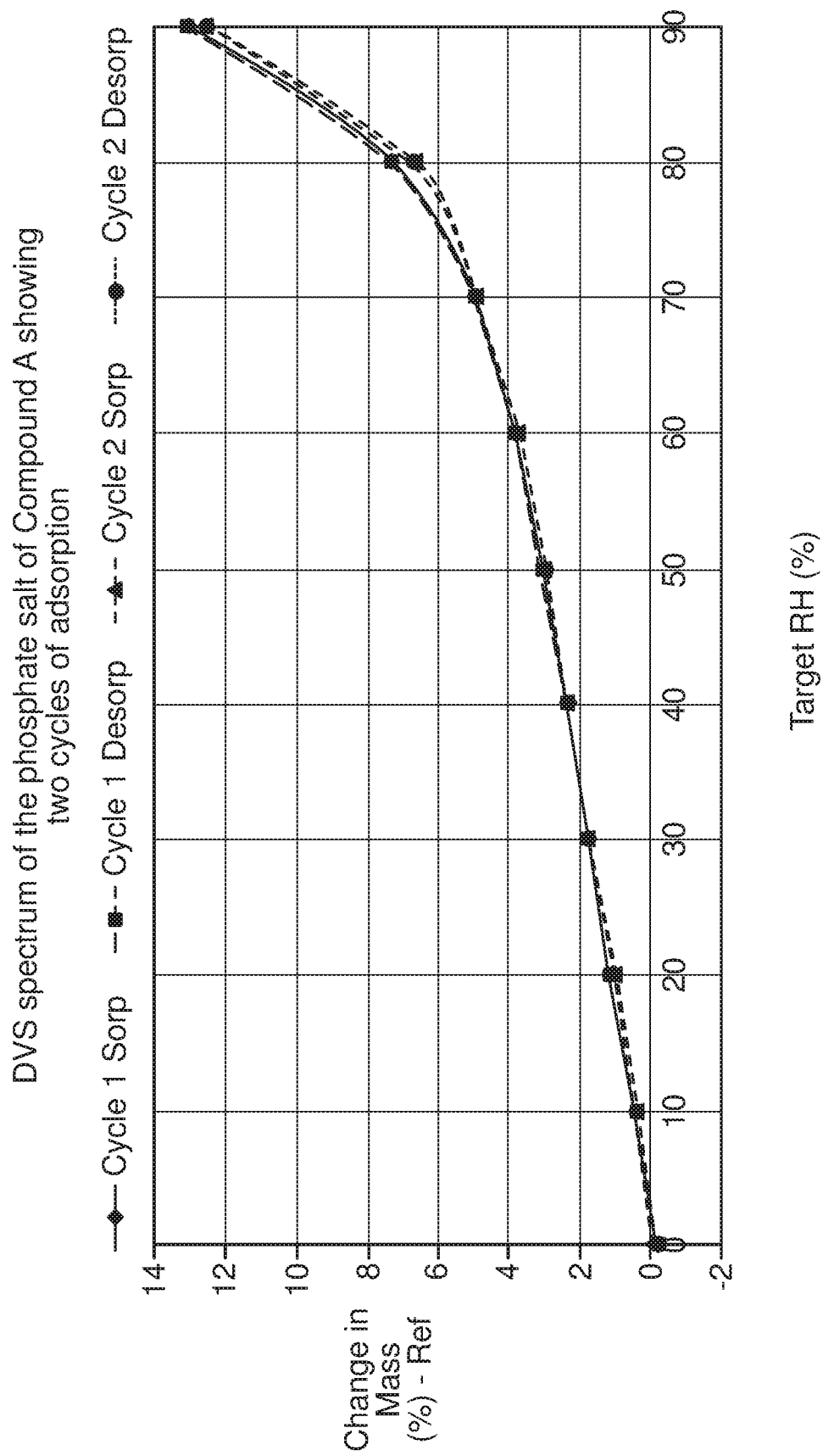
FIG. 38 is a DVS spectrum of the phosphate salt of Compound A showing two cycles of adsorption.

In other embodiments, a phosphate salt of Compound A is provided. In one aspect, the phosphate form of Compound A is crystalline. In a preferred aspect, a crystalline form of a phosphate salt of Compound A produces an X-ray powder diffraction pattern comprising peaks at 6.3, 6.7, and 20.0 degrees two theta±0.2 degrees two theta. The XRPD pattern of a crystalline phosphate salt of Compound A may further comprise one or more of the following peaks: 13.3, 17.0, 17.7, 18.2, or 18.8 degrees two theta±0.2 degrees two theta. A crystalline phosphate salt of Compound A further may be characterized by an XRPD substantially as depicted in FIG. 21. The phosphate salt of Compound A may also be characterized by a DSC thermogram comprising endothermic events with peak temperatures at about 192.3° C. and about 222.2° C. The phosphate salt of Compound A may further be characterized by a DSC thermogram substantially as depicted in FIG. 30. The phosphate salt may also be characterized by a $^1$H-NMR spectrum substantially as depicted in FIG. 12. The phosphate salt additionally may be characterized by a DVS substantially as depicted in FIG. 38. The phosphate salt of Compound A may further be characterized by an X-ray powder diffraction pattern comprising those peaks identified in Table 1, wherein the relative intensity of the peaks is greater than about 2%, more preferably greater than about 5%, more preferably greater than about 10%.

Figure 13:
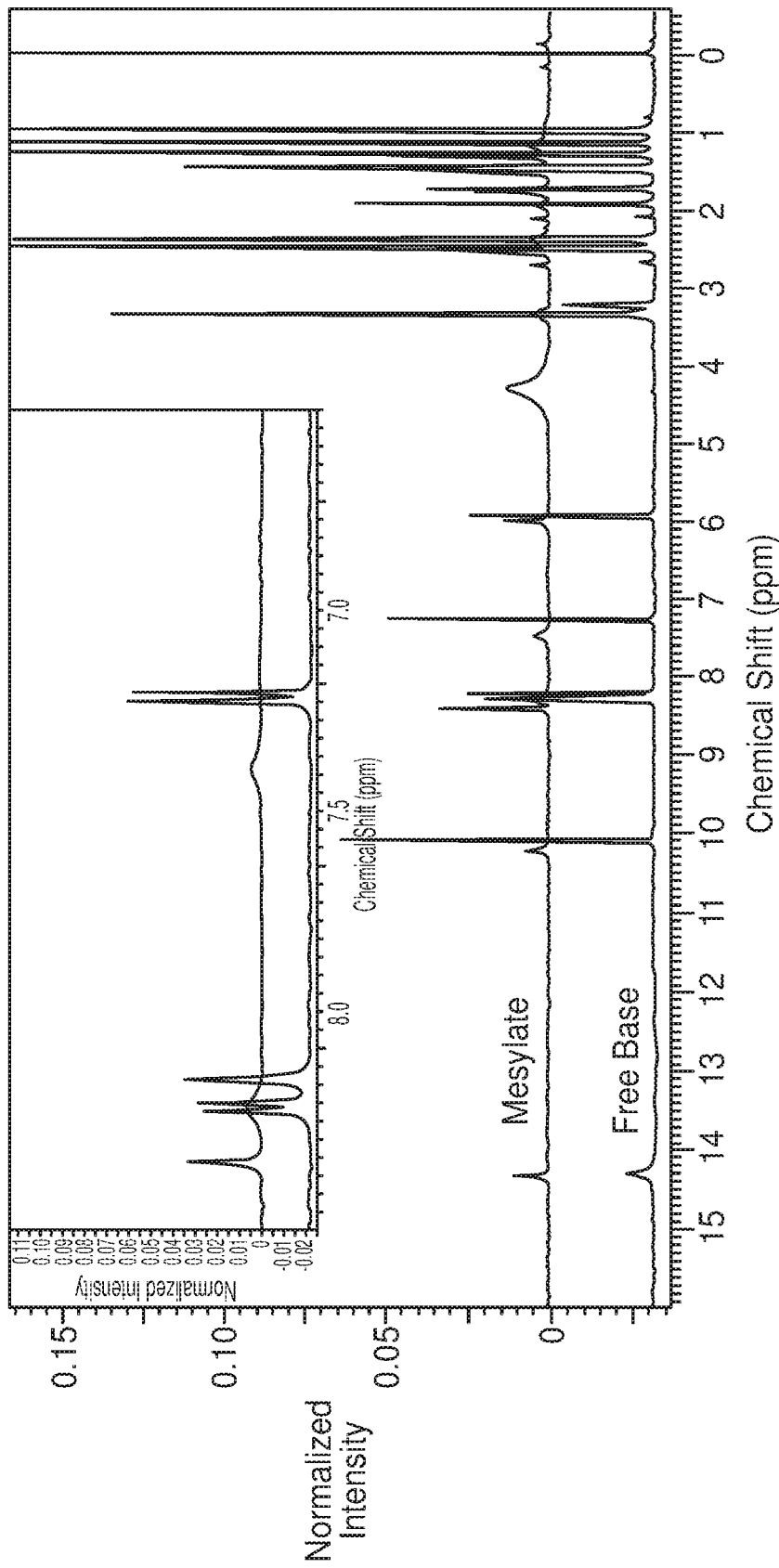
Figure 22:
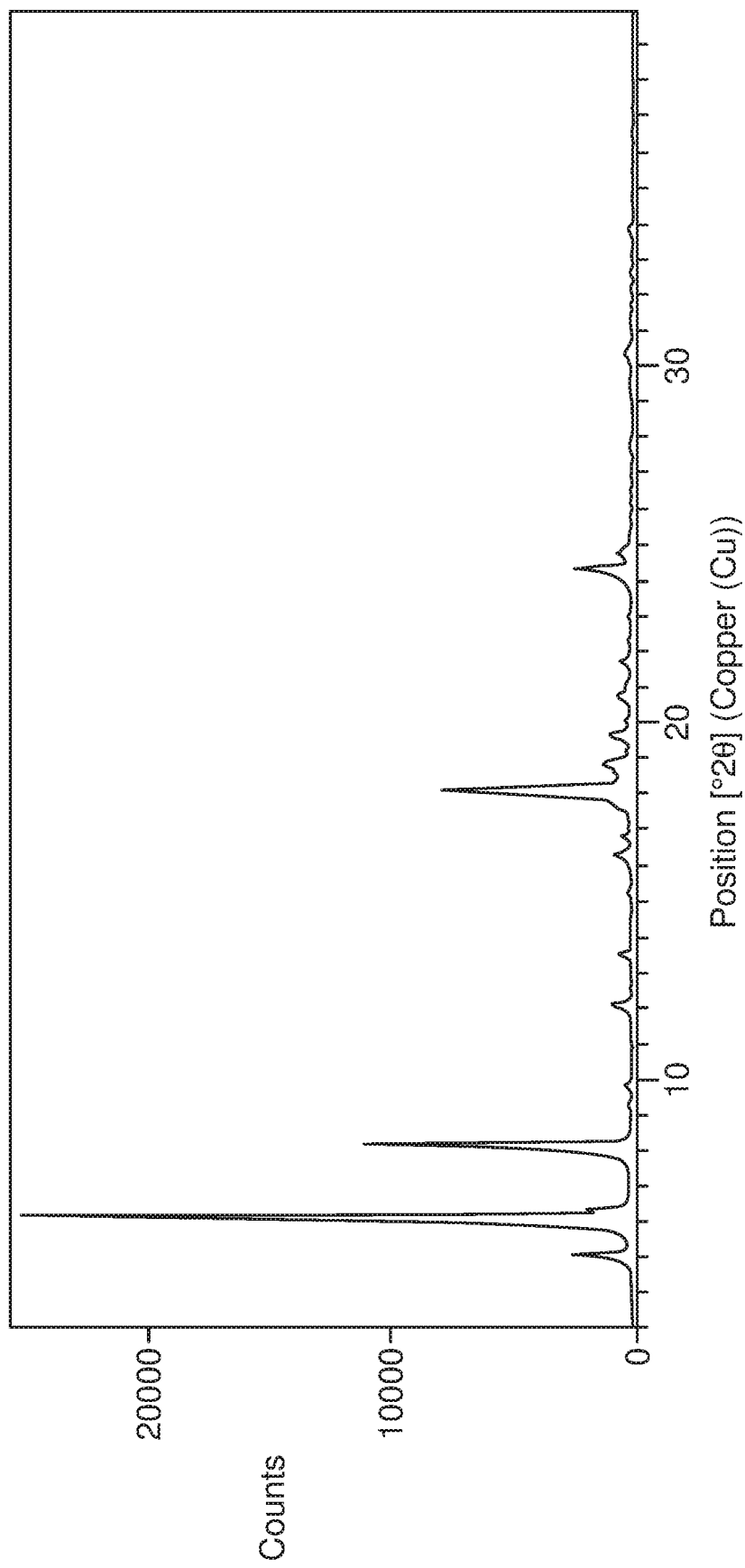
Figure 31:
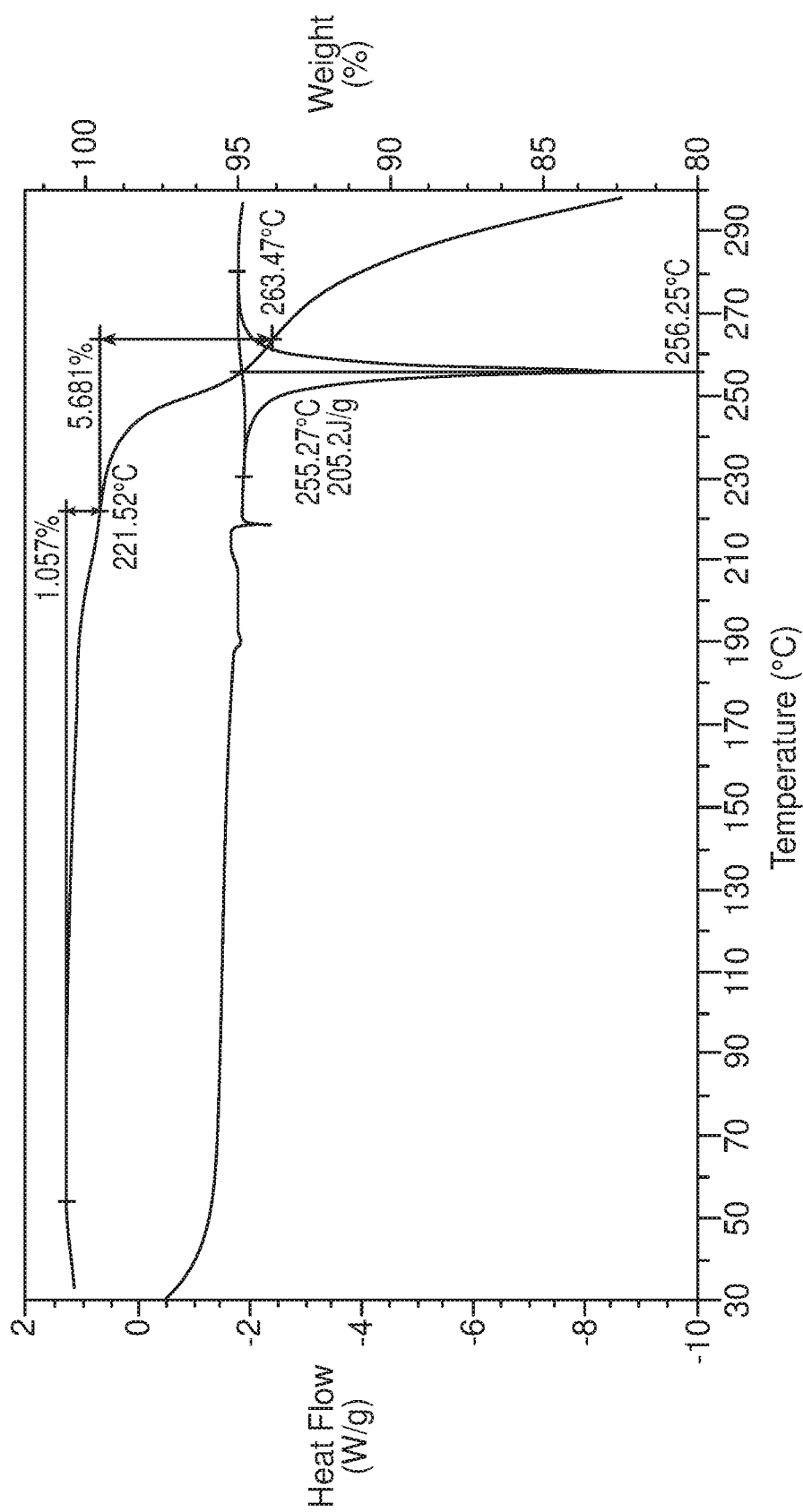

In further embodiments, a mesylate salt of Compound A is provided. In some aspects, the mesylate salt of Compound A is crystalline. A crystalline form of a mesylate salt of Compound A may produce an XRPD pattern comprising peaks at 6.0, 8.1 and 18.1 degrees two theta±0.2 degrees two theta. A crystalline form of a mesylate salt of Compound A may produce an XRPD pattern further comprising one or more of the following peaks: 5.0, 6.3, 18.9, or 24.3 degrees two theta±0.2 degrees two theta. A crystalline mesylate salt of Compound A may also be characterized by an XRPD pattern substantially as depicted in FIG. 22. The mesylate salt may further be characterized by a DSC thermogram comprising an endotherm with a peak temperature at about 256.3° C. The mesylate salt may also be characterized by a DSC thermogram substantially as depicted in FIG. 31. The mesylate salt may further be characterized by a solution $^1$H-NMR spectrum of FIG. 13. The mesylate salt of Compound A may further be characterized by an X-ray powder diffraction pattern comprising those peaks identified in Table 2, wherein the relative intensity of the peaks is greater than about 2%, preferably greater than about 5%, more preferably greater than about 10%, more preferably greater than about 25%.

Figure 14:
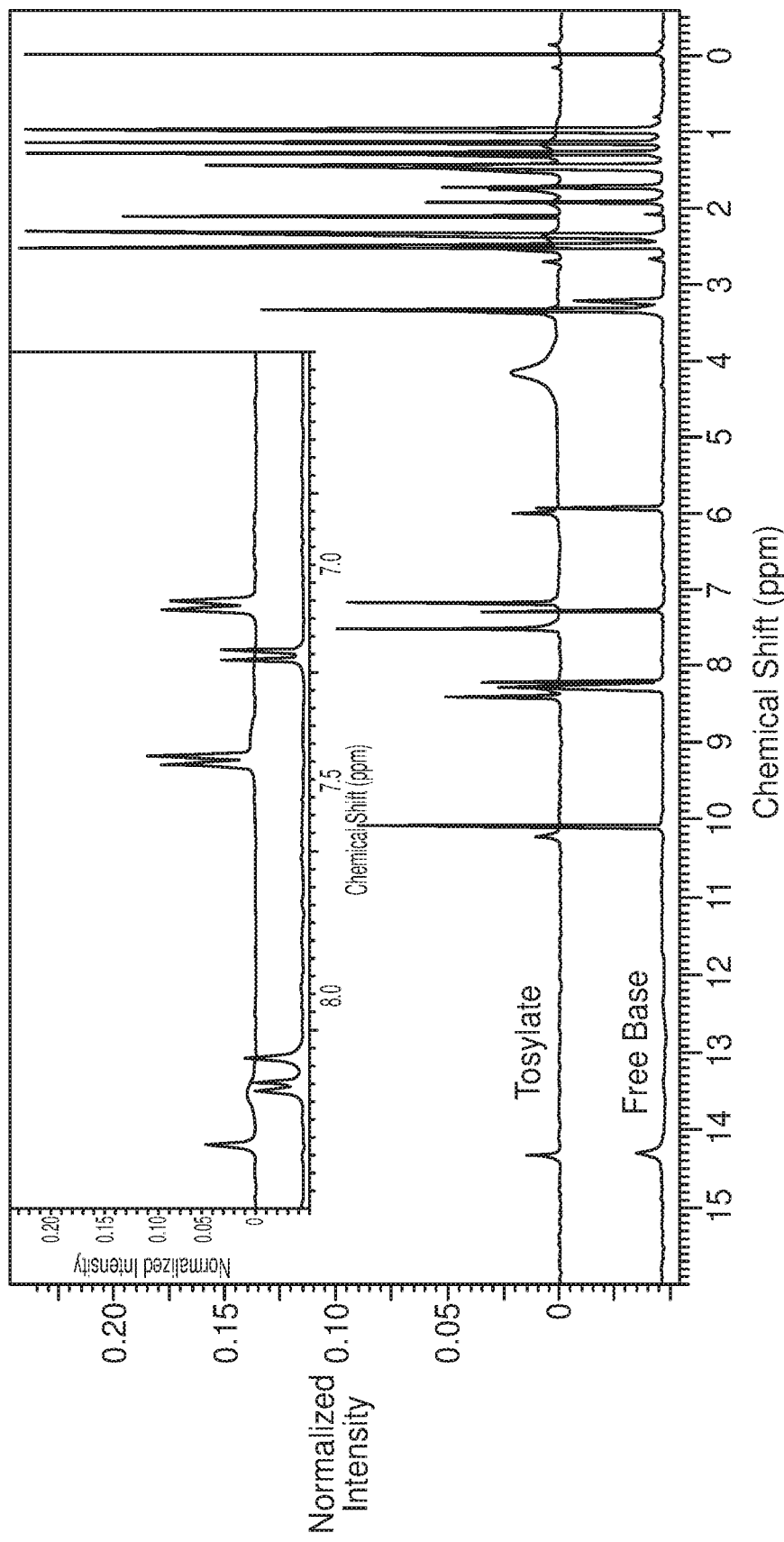
Figure 23:
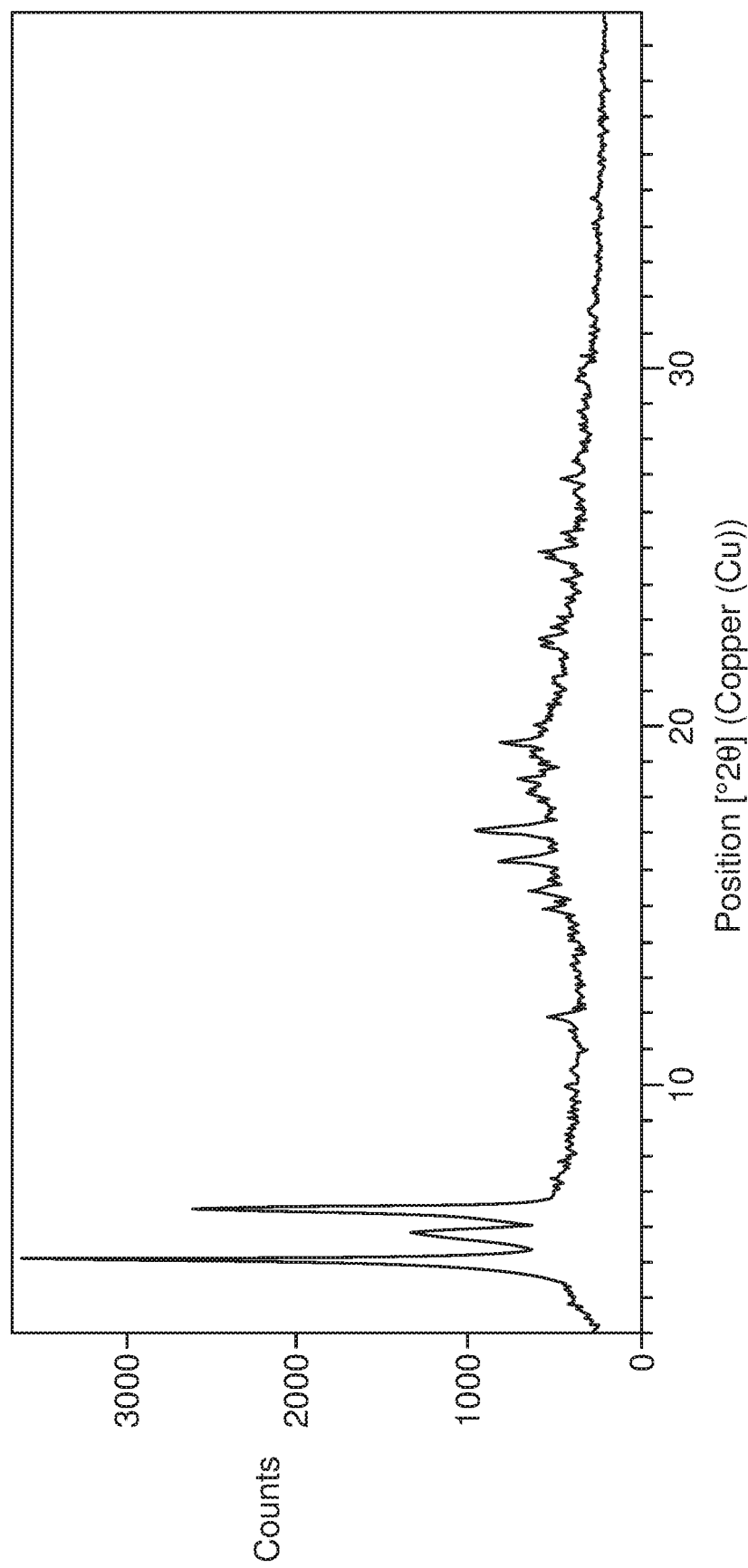
Figure 32:
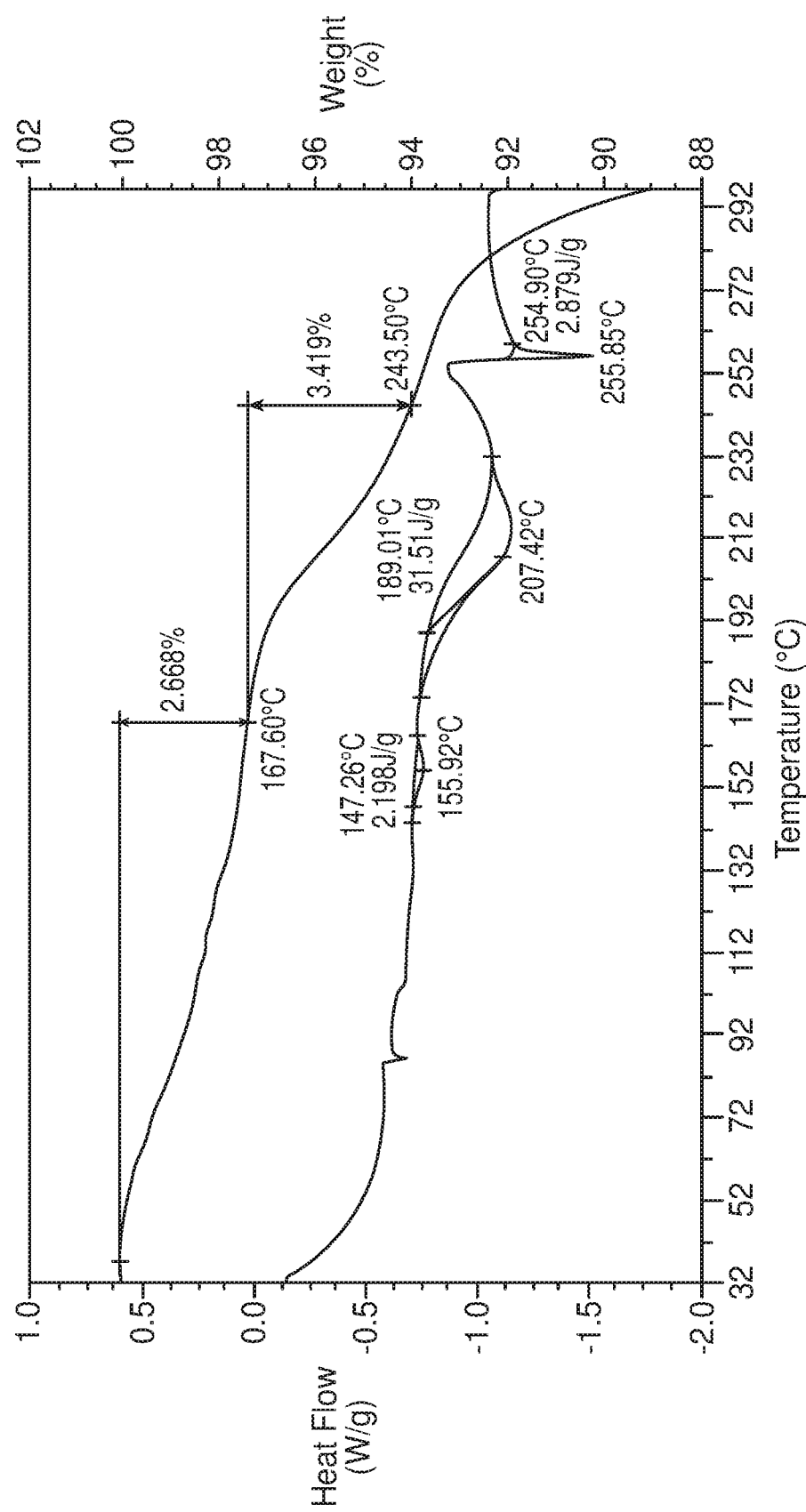

In some aspects, the tosylate salt form of Compound A is crystalline. A crystalline tosylate salt of Compound A may produce an XRPD pattern comprising peaks at 5.1, 6.4 and 6.5 degrees two theta±0.2 degrees two theta. A crystalline tosylate salt of Compound A may produce an XRPD pattern that further comprises one or more of the following peaks: 5.8, 5.9, 16.3, 17.2, or 19.6 degrees two theta±0.2 degrees two theta. A crystalline tosylate salt of Compound A may also be characterized by an XRPD pattern substantially as depicted in FIG. 23. The tosylate salt may further characterized by a DSC thermogram comprising endothermic events with peak temperatures at about 155.9° C., about 207.4° C. and about 255.9° C. The tosylate salt may also be characterized by a DSC thermogram substantially as depicted in FIG. 32. The tosylate salt may further be characterized by a solution $^1$H-NMR spectrum of FIG. 14. The tosylate salt of Compound A may further be characterized by an X-ray powder diffraction pattern comprising those peaks identified in Table 3, wherein the relative intensity of the peaks is greater than about 2%, more preferably greater than about 5%, preferably greater than about 10%, more preferably greater than about 25%, more preferably greater than about 50%.

Figure 15:
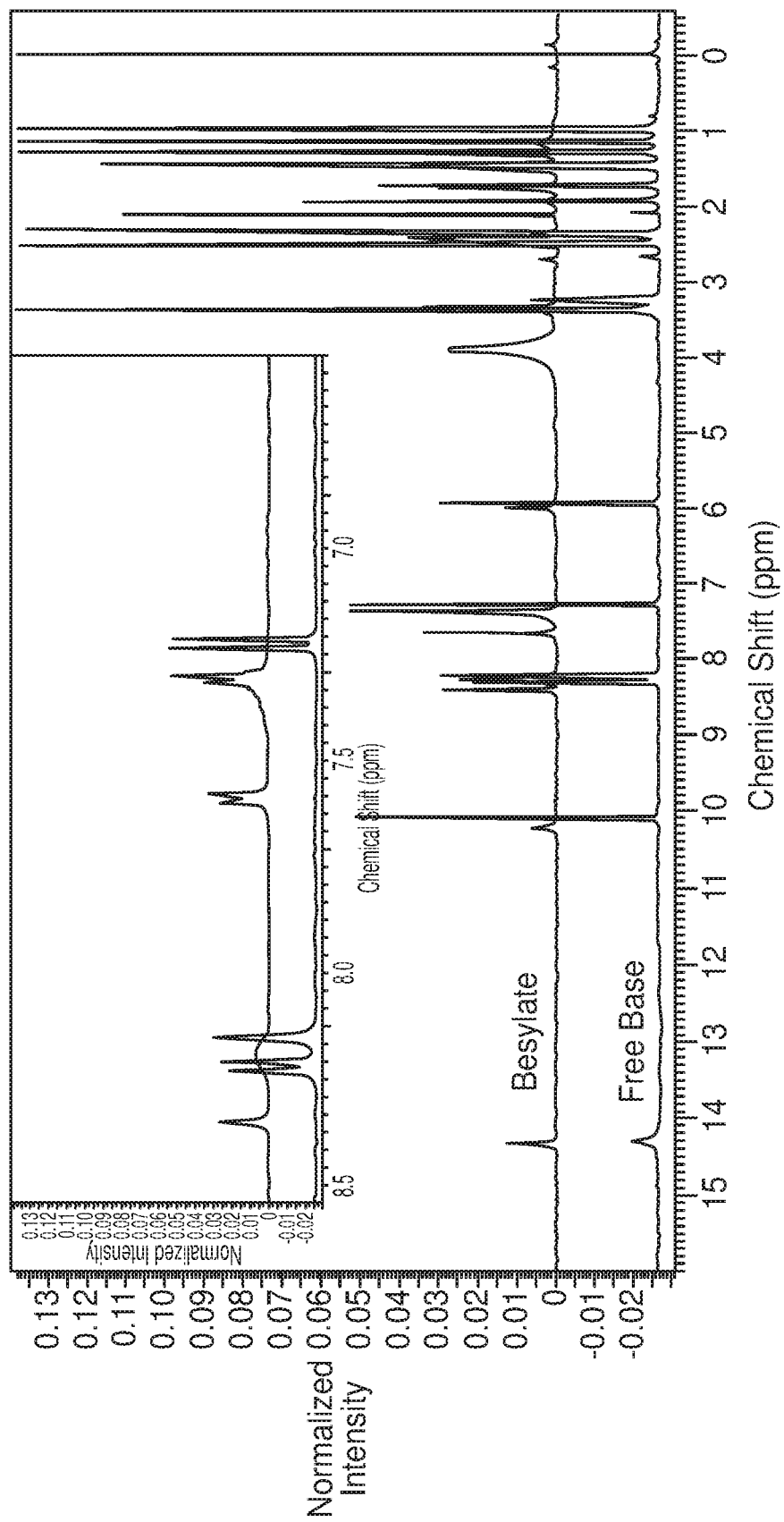
Figure 24:
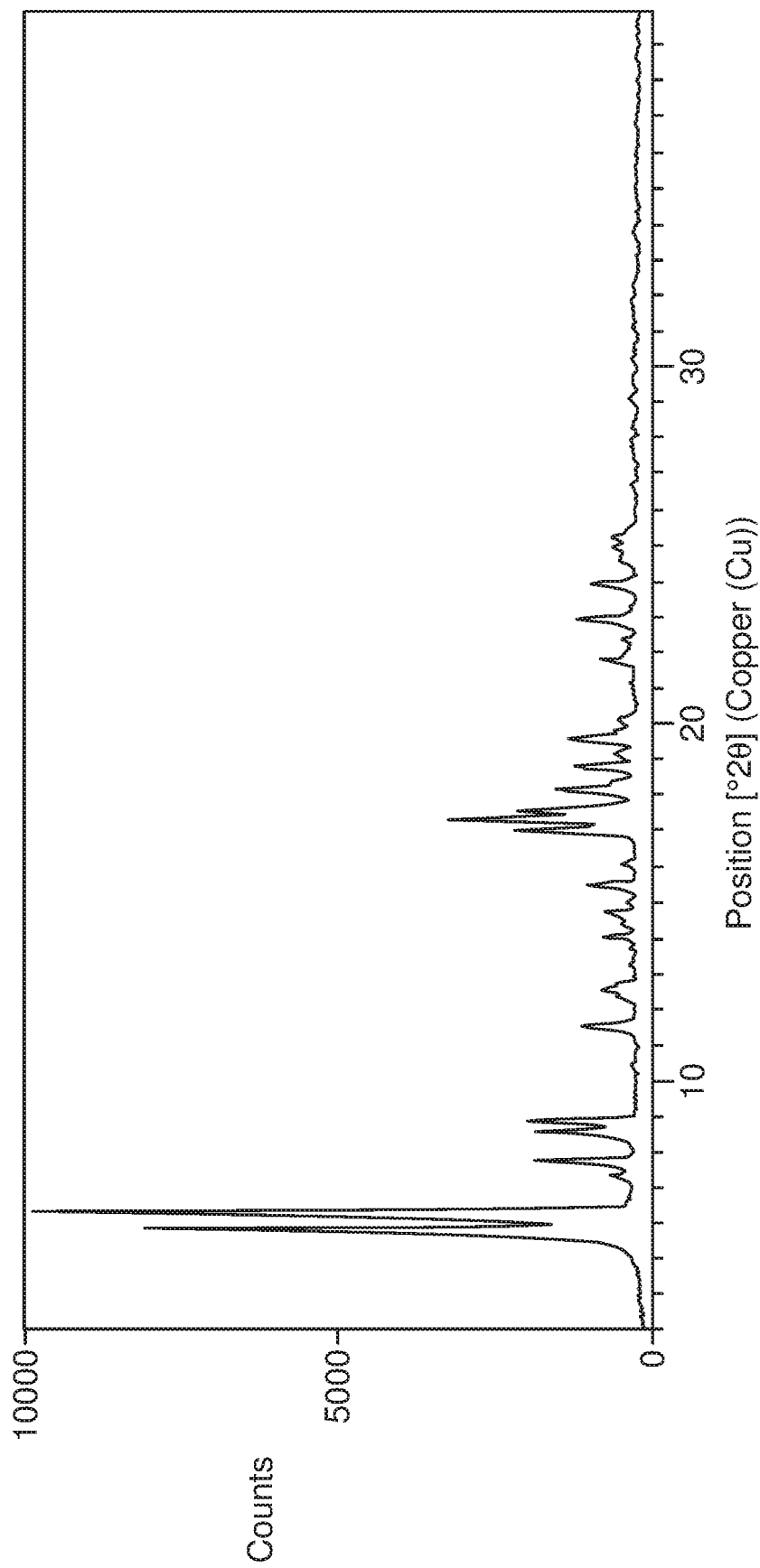
Figure 33:
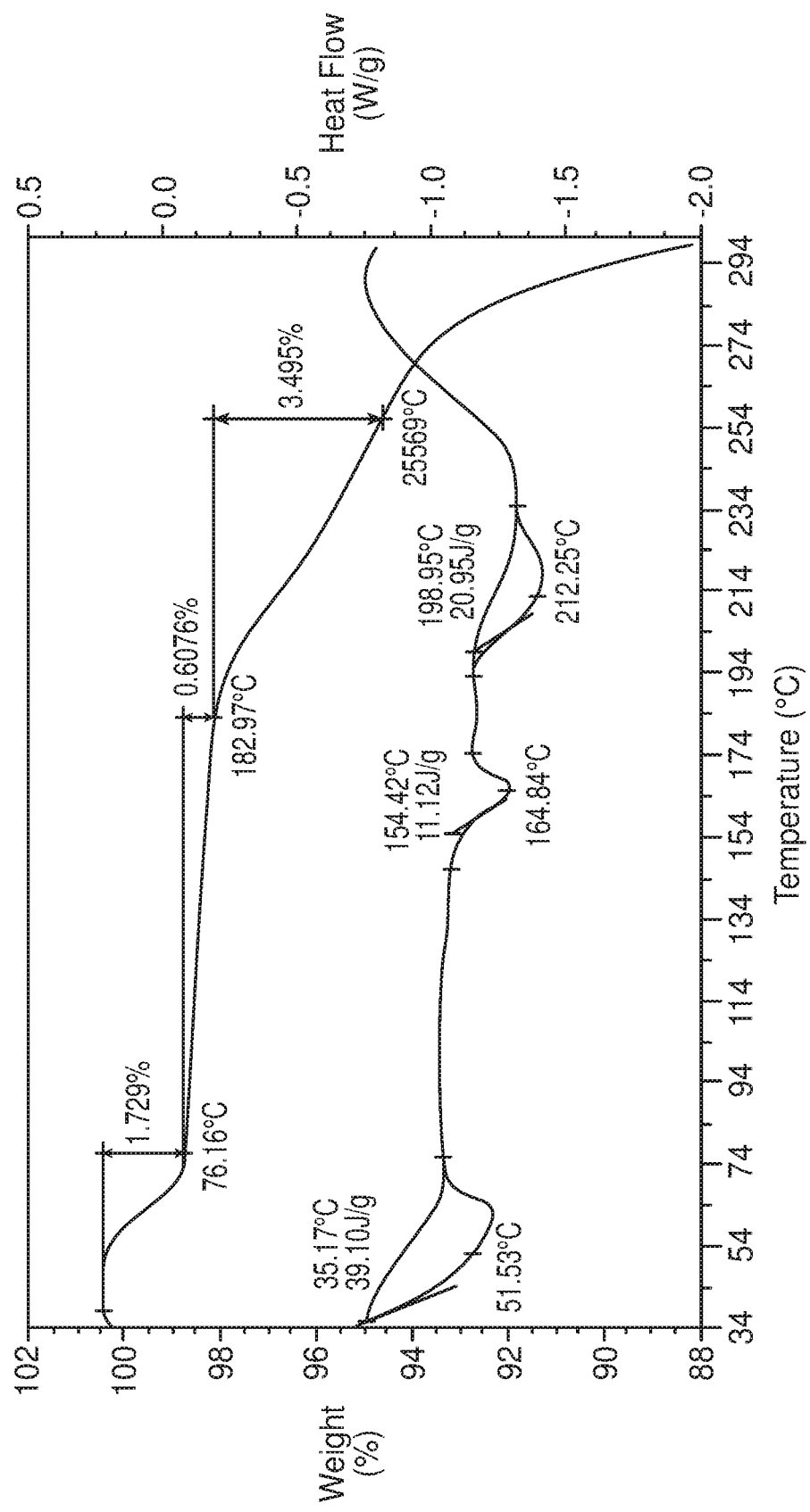

In still further embodiments, a besylate salt of Compound A is provided. In some aspects, the besylate salt of Compound A is crystalline. In some aspects, a crystalline form of a besylate salt of Compound A may produce an XRPD pattern comprising peaks at 5.8, 6.3, 17.1, 17.4, and 17.6 degrees two theta±0.2 degrees two theta. The XRPD pattern of a crystalline besylate salt may further comprise one or more of the following peaks: 7.8, 8.6, 8.9, 18.2, 18.9, 19.6 or 23.0 degrees two theta±0.2 degrees two theta. A crystalline besylate salt of Compound A may be further characterized by an XRPD pattern substantially as depicted in FIG. 24. The besylate salt of Compound A may also be characterized by a DSC thermogram comprising endothermic events with peak temperatures at about 51.5° C., about 164.8° C., and about 212.2° C. The besylate salt of Compound A may be further characterized by a DSC spectrum substantially as depicted in FIG. 33. The besylate salt of Compound A may also be characterized by a solution $^1$H-NMR spectrum of FIG. 15. The besylate salt of Compound A may further be characterized by an X-ray powder diffraction pattern comprising those peaks identified in Table 4, wherein the relative intensity of the peaks is greater than about 2%, preferably greater than about 5%, more preferably greater than about 10%, more preferably greater than about 25%.

Figure 16:
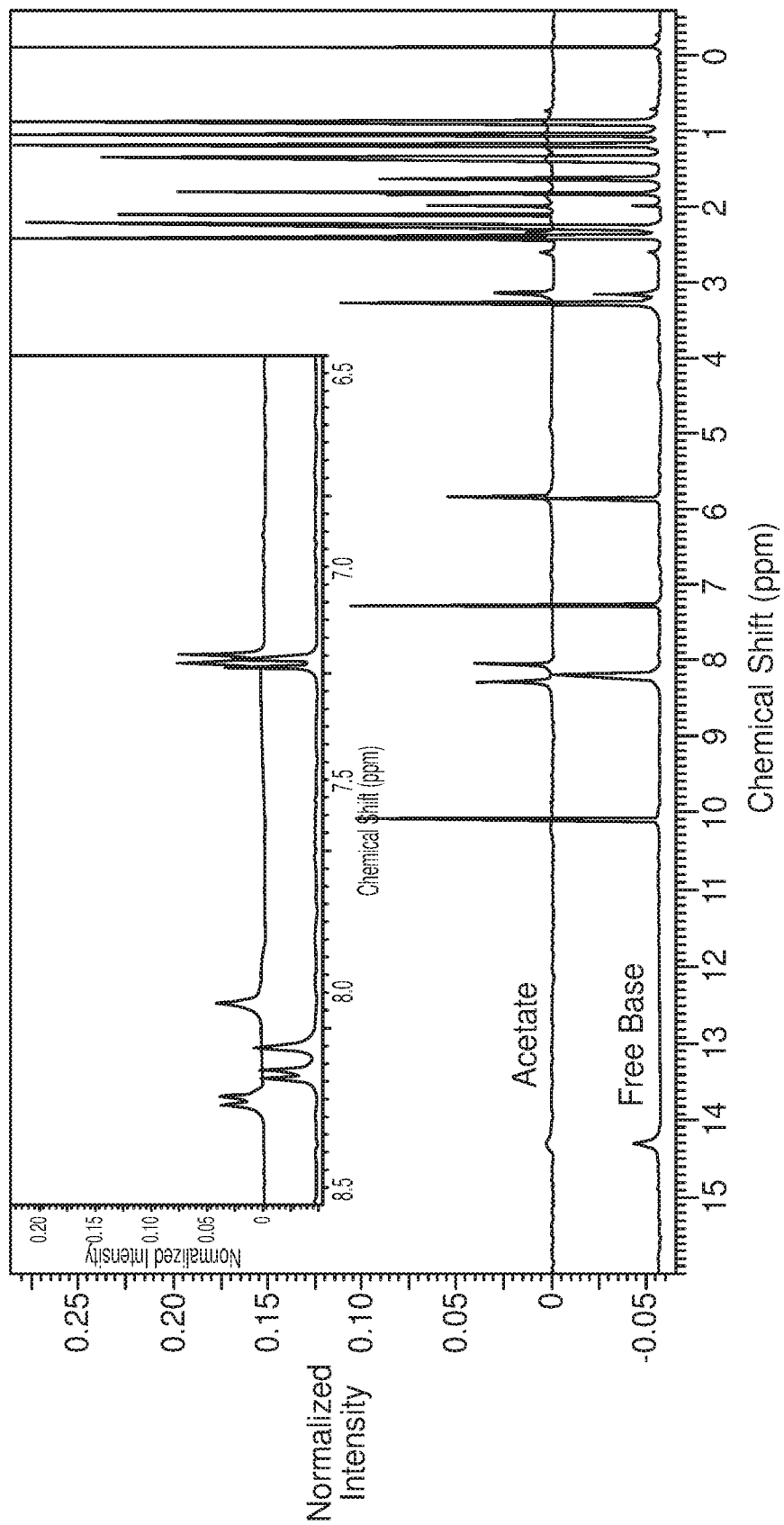
Figure 25:
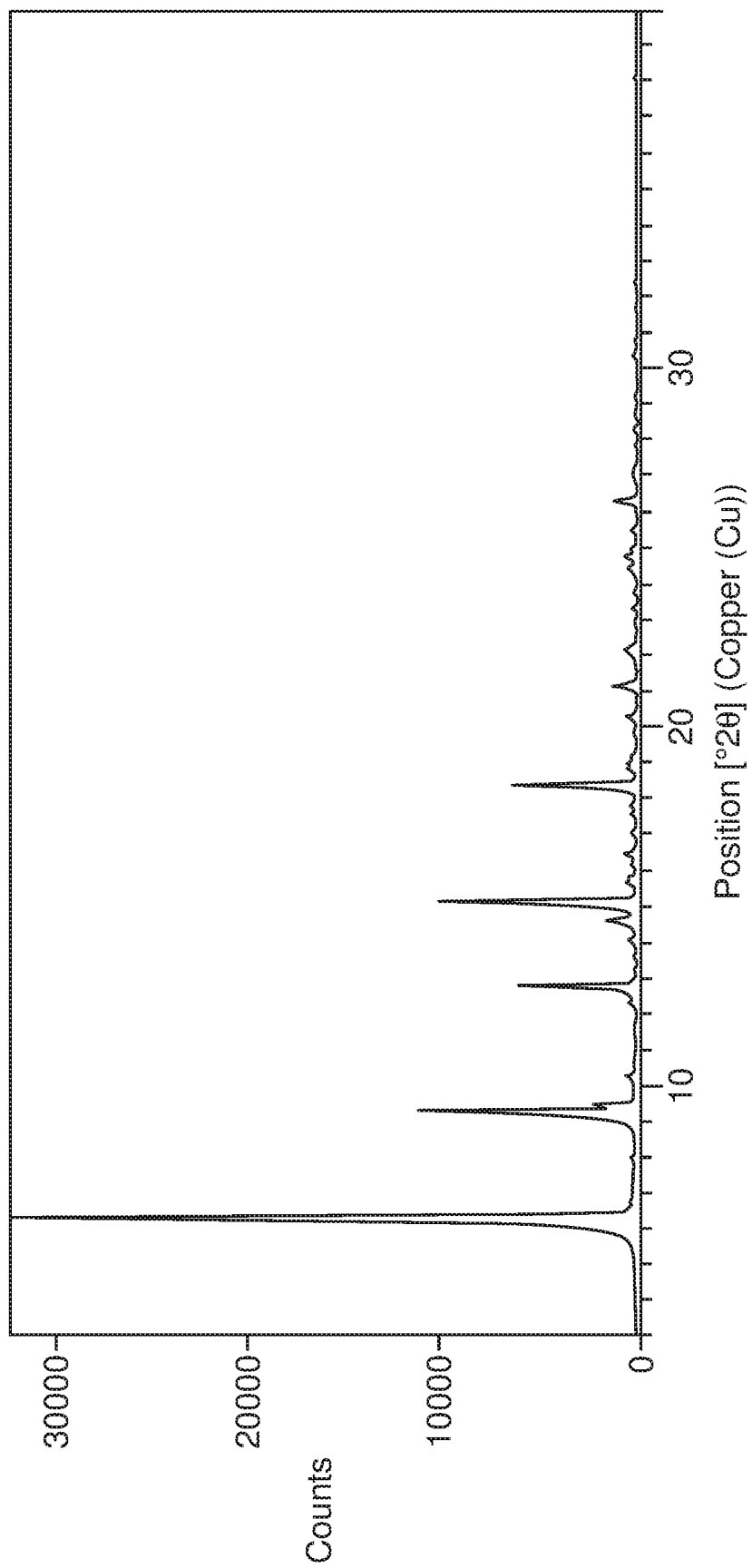
Figure 34:
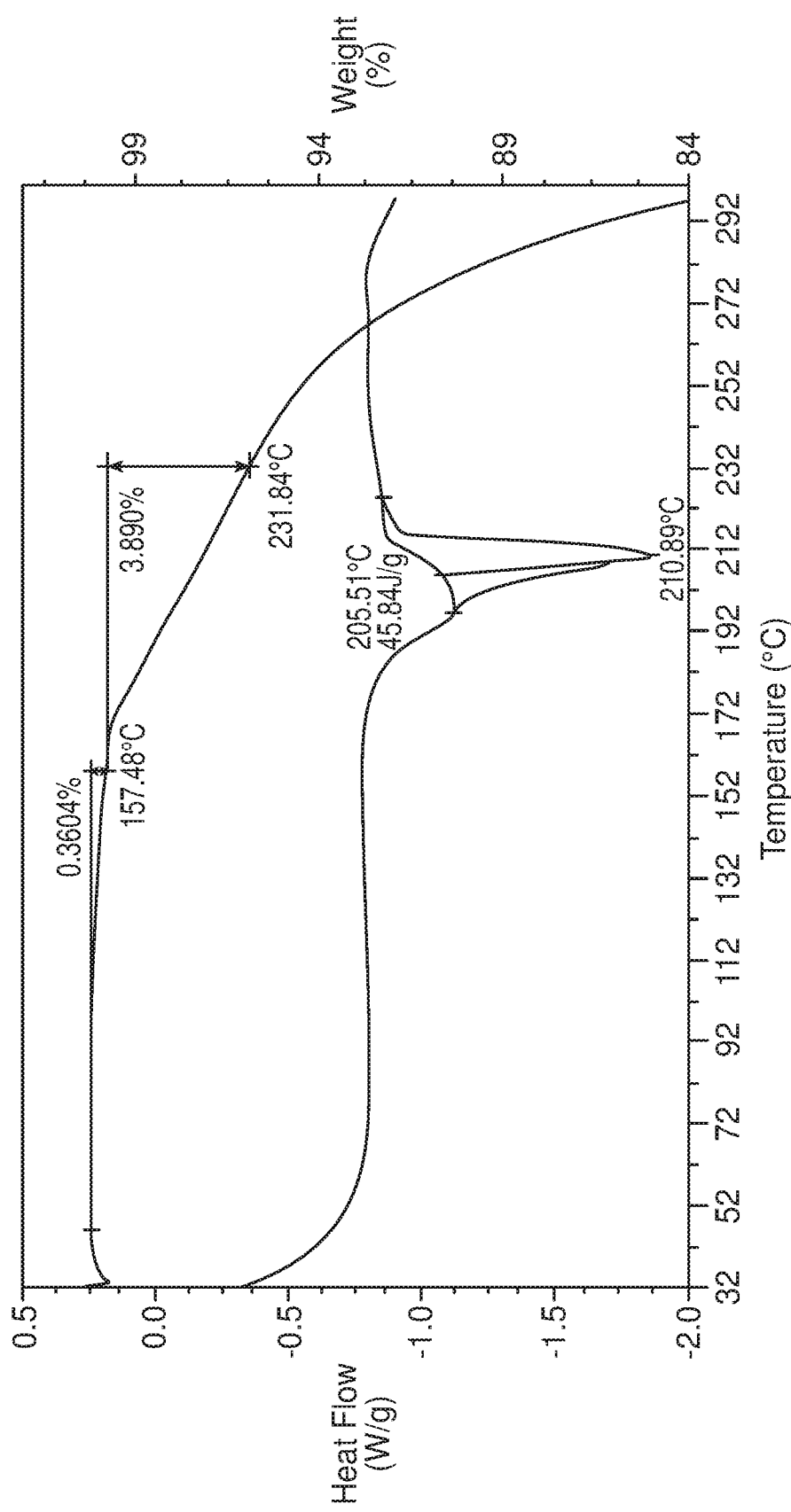

In some aspects, an acetate solid residue of Compound A is provided. The acetate solid residue (i.e. the solid residue isolated from the screening experiment with acetic acid) showed a pattern similar to Compound A, as shown in FIG. 25. In some aspects, the acetate solid residue of Compound A is crystalline. A crystalline acetate solid residue of Compound A may produce an XRPD pattern having at least three peaks at 6.1, 6.3, 9.2, 12.7, 15.1, and 18.4 degrees two theta±0.2 degrees two theta. The XRPD pattern of a crystalline acetate salt of Compound A may further comprise one or more of the following peaks: 9.4 or 14.6 degrees two theta±0.2 degrees two theta. A crystalline acetate salt of Compound A may also be characterized by an XRPD pattern substantially as depicted in FIG. 25. A DSC thermogram of the acetate experiment solid residue exhibited an endothermic event with a peak temperature at about 210.9° C., as shown in FIG. 34. The acetate solid residue exhibited a solution $^1$H-NMR spectrum as shown in FIG. 16. The acetate solid residue of Compound A may further be characterized by an X-ray powder diffraction pattern comprising those peaks identified in Table 5, wherein the relative intensity of the peaks is greater than about 2%, preferably greater than about 5%, more preferably greater than about 10%.

Figure 17:
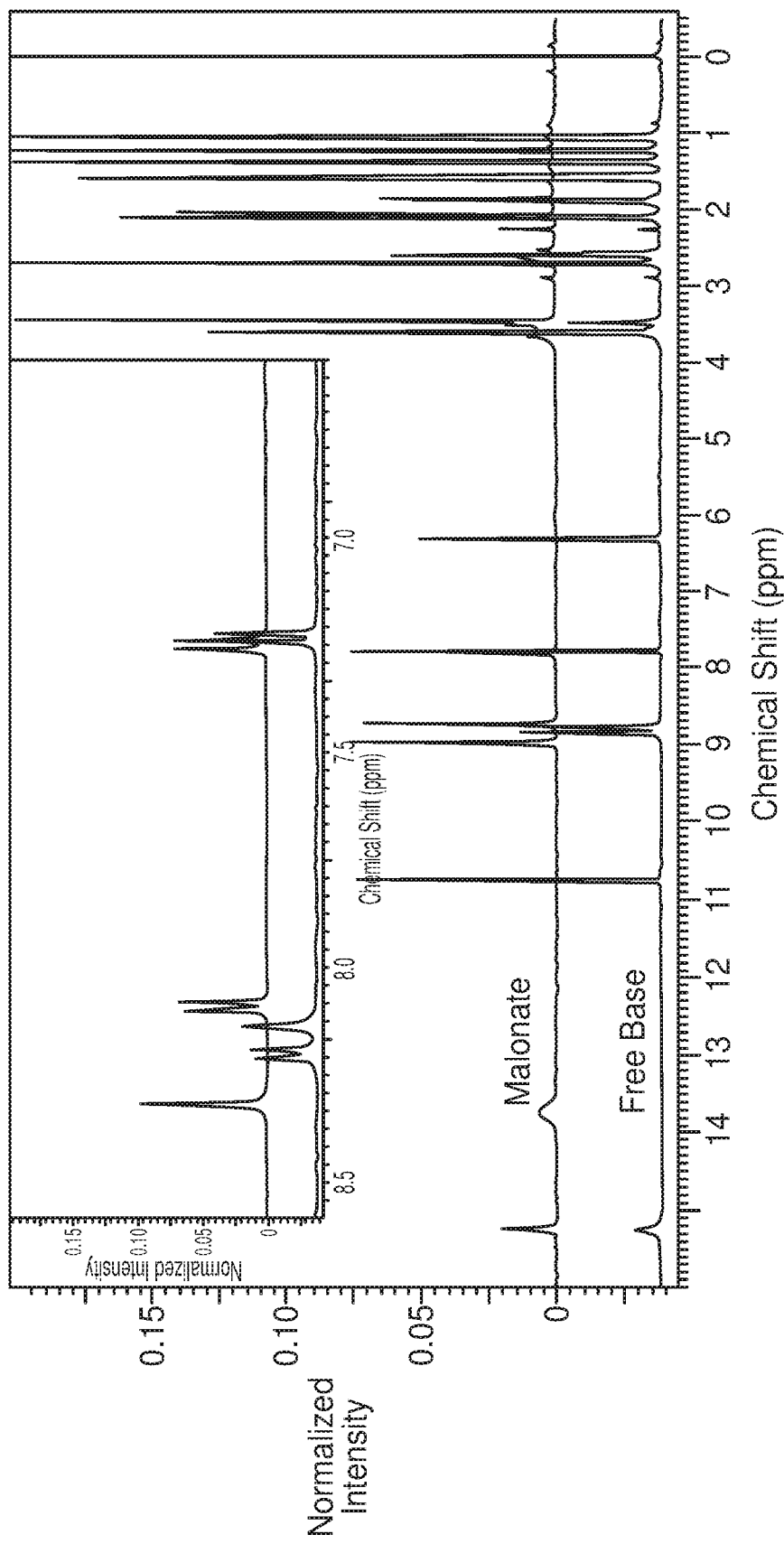
Figure 26:
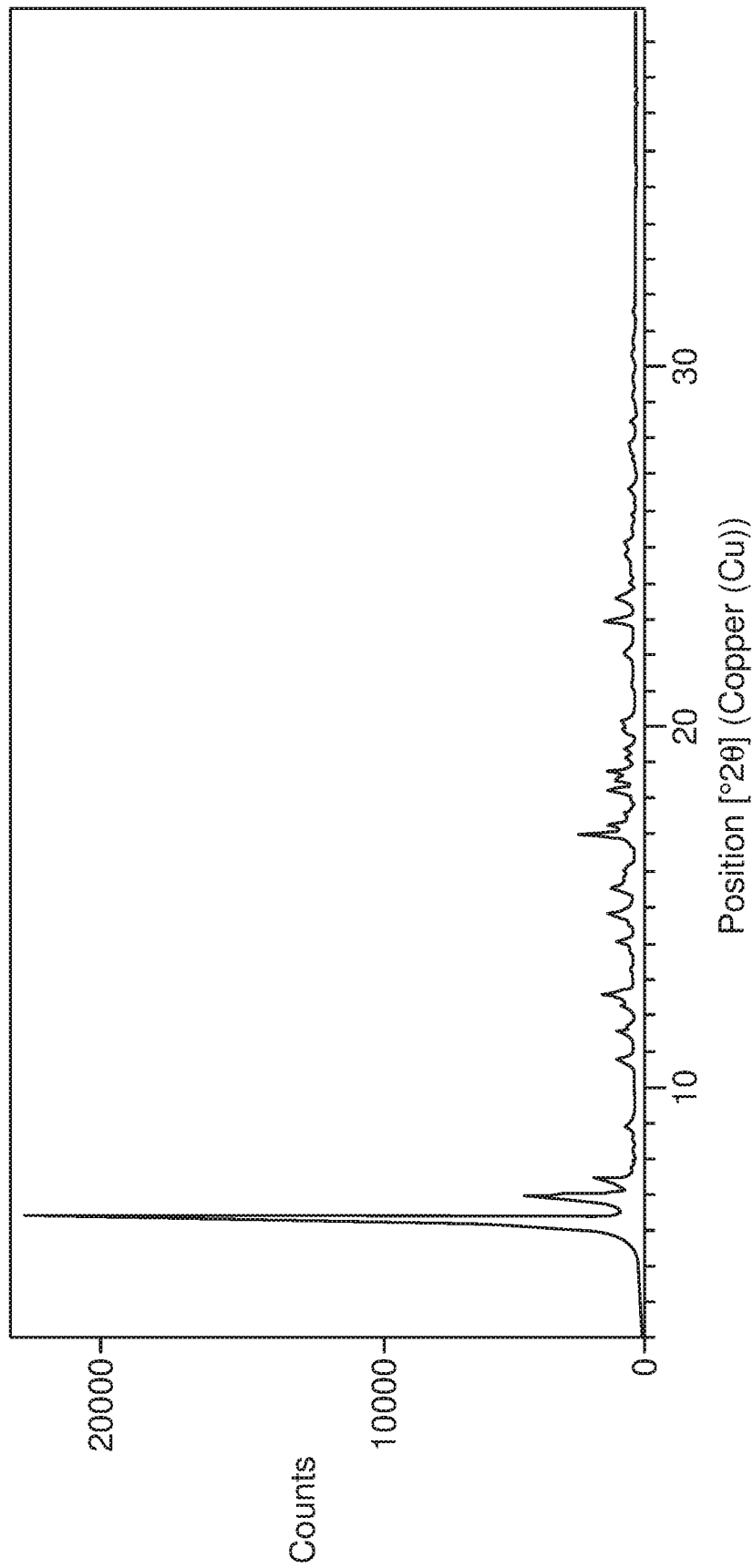
Figure 35:
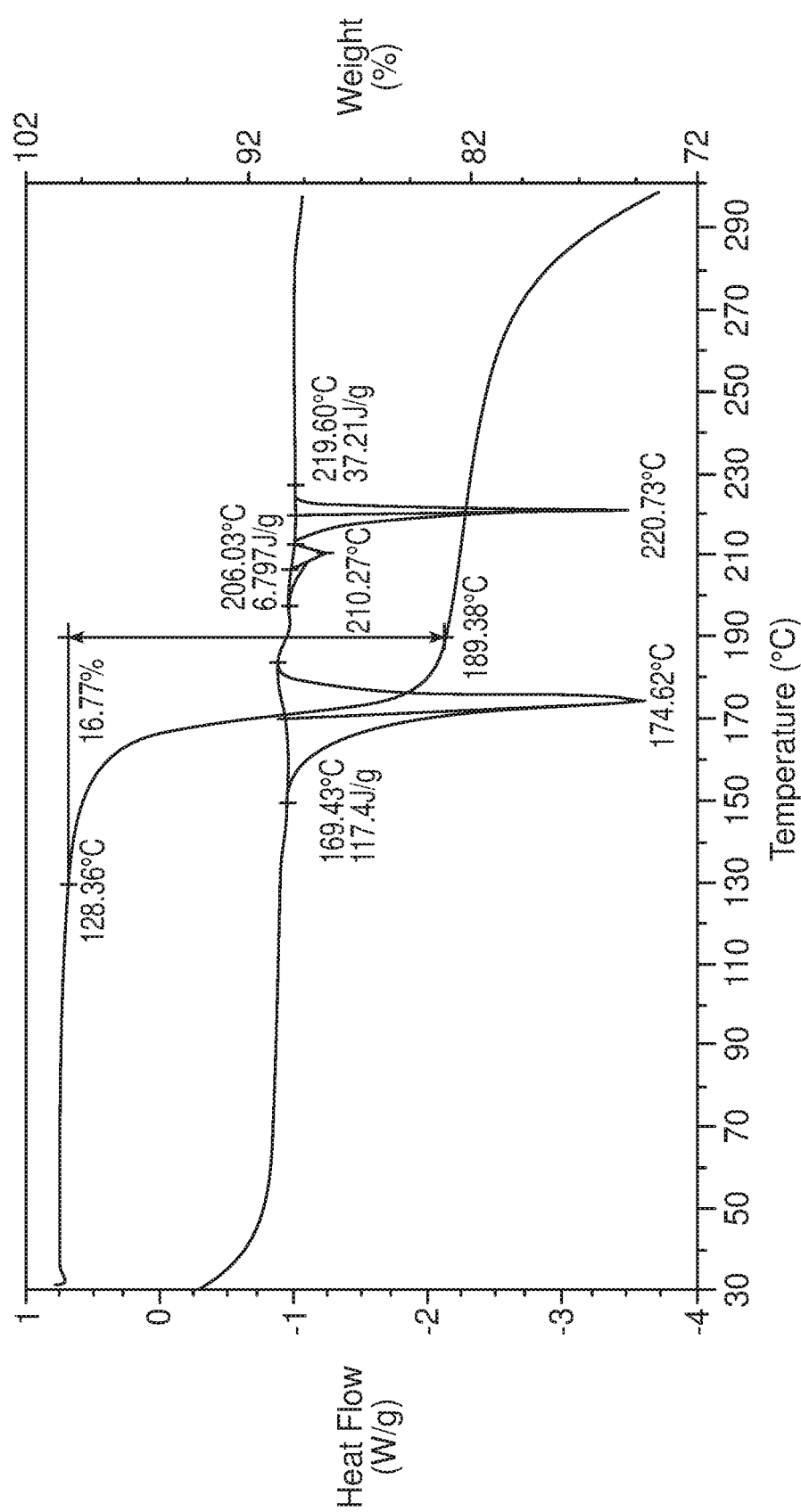

In some aspects, a malonate solid residue of Compound A is provided. The malonate solid residue (i.e. the solid residue isolated from the screening experiment with malonic acid) showed a pattern similar to Compound A, as shown in FIG. 26. In some aspects, the malonate solid residue of Compound A is crystalline. A crystalline malonate solid residue of Compound A may be characterized by an XRPD pattern comprising peaks at 6.3, 6.9, and 17.0 degrees two theta±0.2 degrees two theta. The XRPD pattern of a crystalline malonate salt of Compound A may also comprise one or more of the following peaks: 7.4, 12.5, 18.8 or 23.0 degrees two theta±0.2 degrees two theta. A crystalline malonate solid residue of Compound A may also be characterized by an XRPD pattern substantially as depicted in FIG. 26. The DSC thermogram of the malonate solid residue exhibited endothermic events with peak temperatures at about 174.6°, about 210.3° C., and about 220.7° C., as shown in FIG. 35. The malonate solid residue exhibited a solution $^1$H-NMR spectrum as shown in FIG. 17. The malonate solid residue of Compound A may further be characterized by an X-ray powder diffraction pattern comprising those peaks identified in Table 6, wherein the relative intensity of the peaks is greater than about 2%, preferably greater than about 5%, more preferably greater than about 10%.

Figure 18:
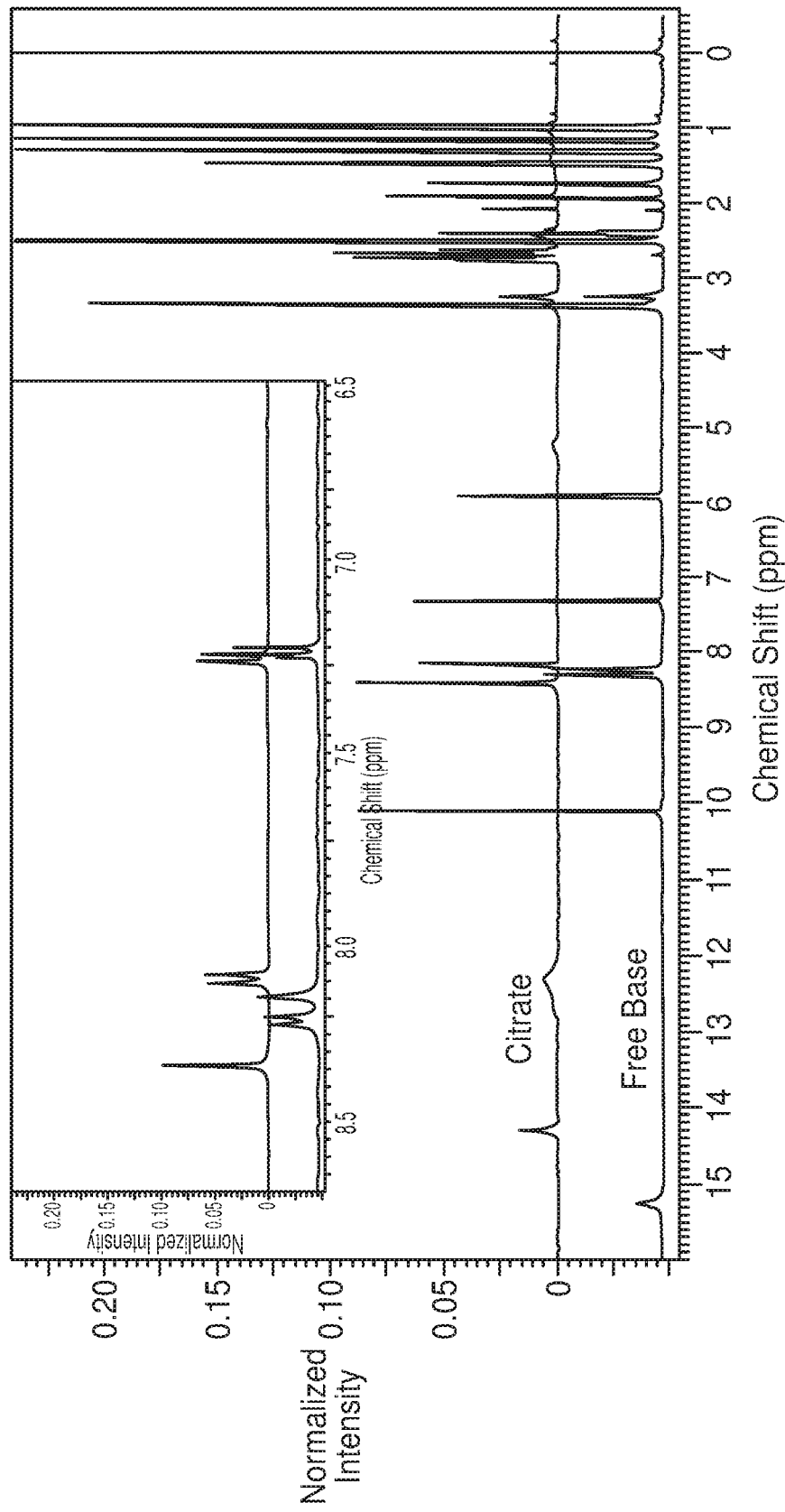
Figure 27:
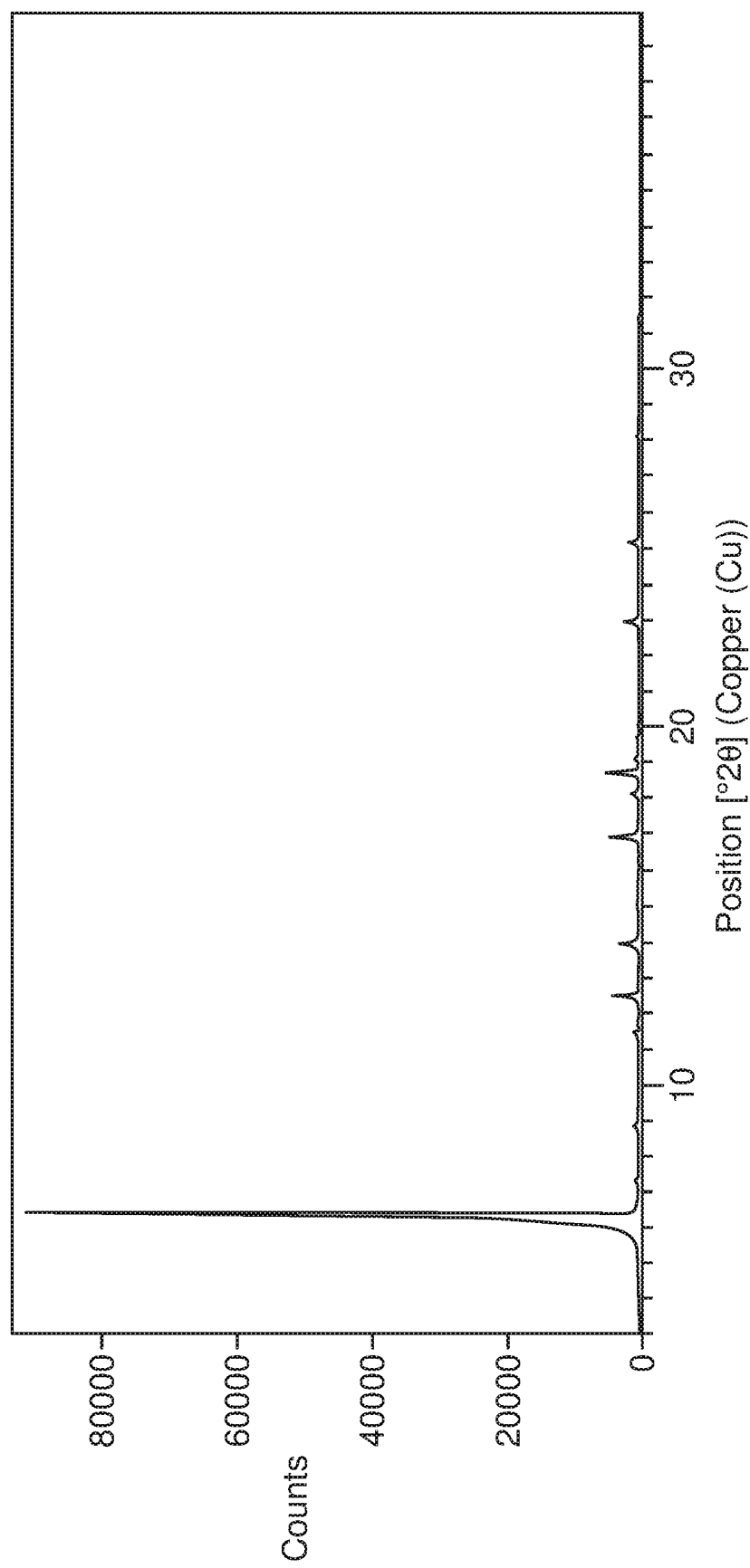
Figure 36:
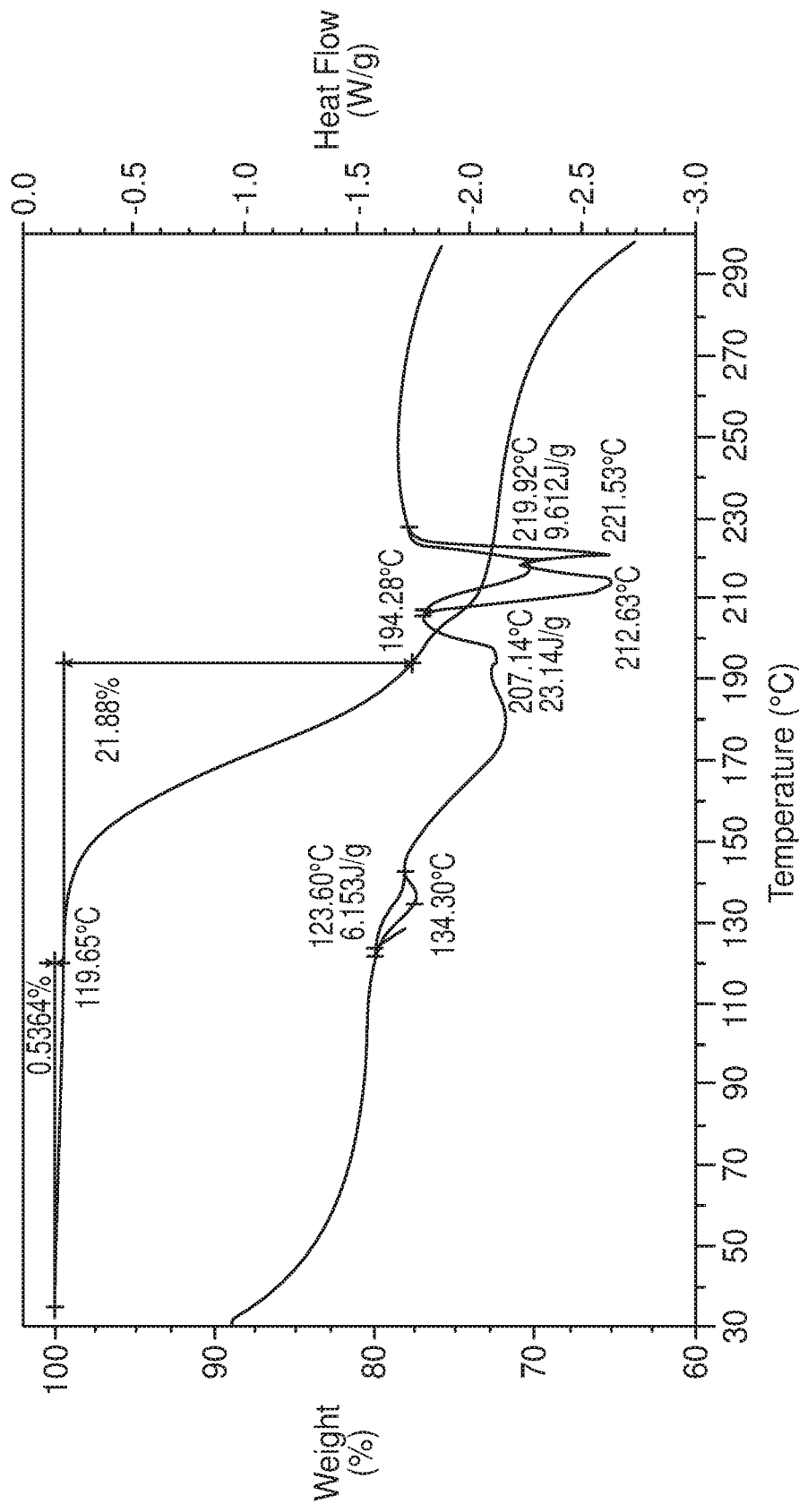

In some aspects, a citrate solid residue of Compound A is provided. The citrate solid residue (i.e. the solid residue isolated from the screening experiment with citric acid) showed a pattern similar to Compound A, as shown in FIG. 27. In some aspects, the citrate solid residue of Compound A is in a crystalline form. A crystalline citrate solid residue of Compound A may be characterized by an XRPD pattern comprising peaks at 6.3, 17.0 and 18.8 degrees two theta±0.2 degrees two theta. The XRPD pattern of a crystalline citrate salt of Compound A may further comprise one or more of the following peaks: 12.5, 14.0 or 23.0 degrees two theta±0.2 degrees two theta. A crystalline citrate salt of Compound A may also be characterized by an XRPD pattern substantially as depicted in FIG. 27. A DSC thermogram of the citrate solid residue exhibited endothermic events with peak temperatures at about 134.3° C., about 212.6° C., and about 221.5° C., as shown in FIG. 36. The citrate solid residue exhibited a solution $^1$H-NMR spectrum as shown in FIG. 18. The citrate solid residue of Compound A may further be characterized by an X-ray powder diffraction pattern comprising those peaks identified in Table 7, wherein the relative intensity of the peaks is greater than about 2%, more preferably greater than about 5%, more preferably greater than about 10%.

Figure 19:
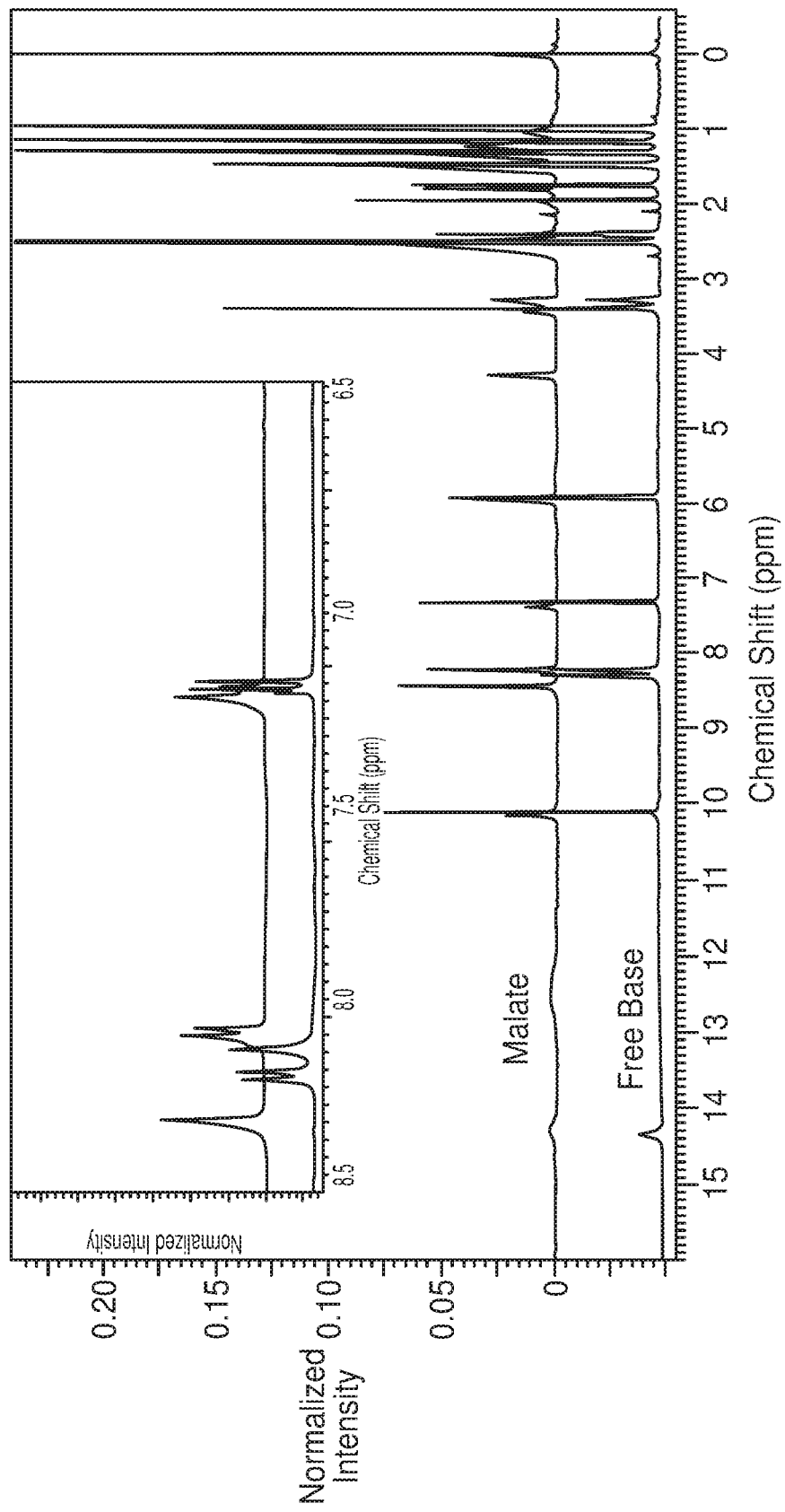
Figure 28:
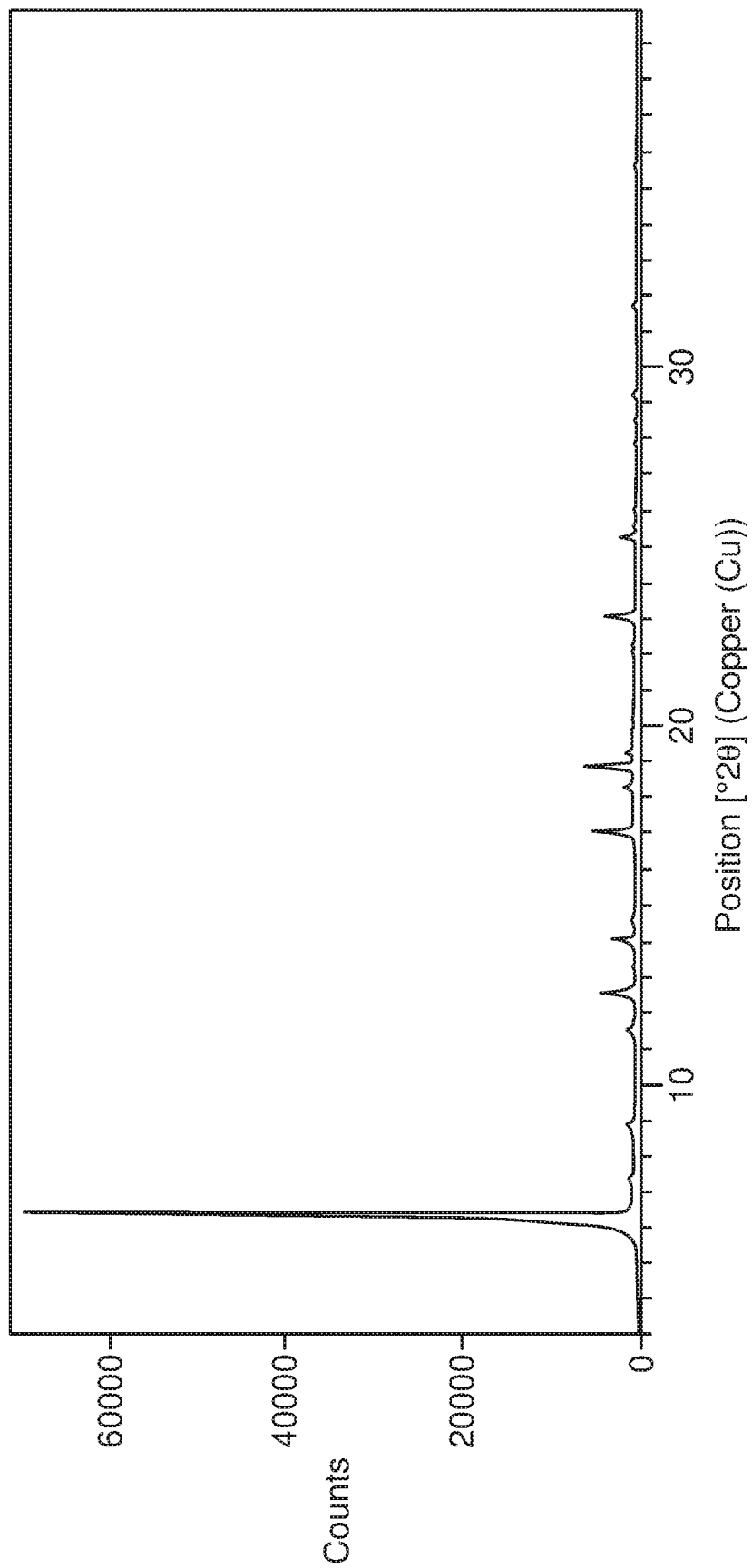
Figure 37:
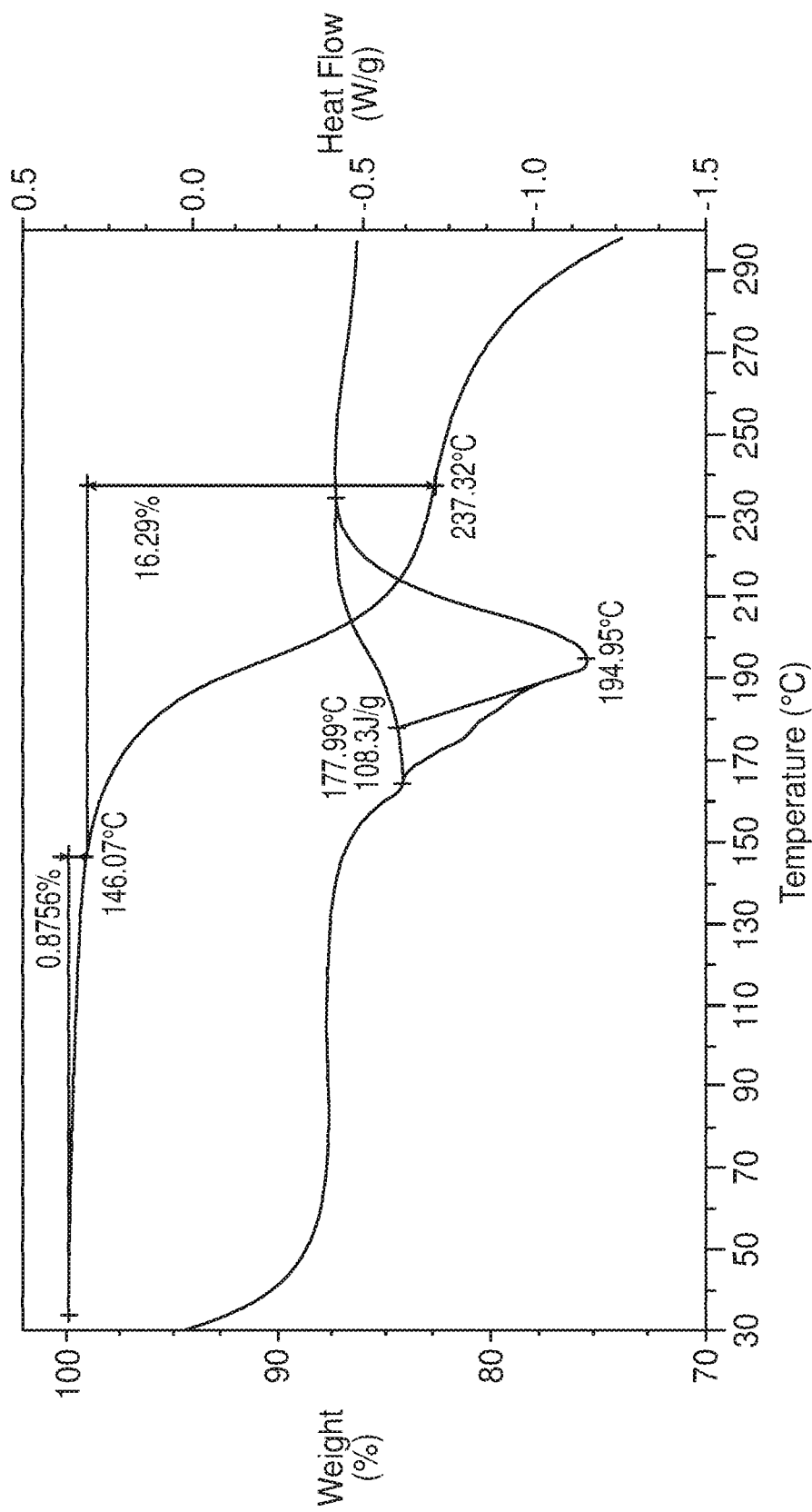

In some aspects, a malate solid residue of Compound A is provided. The malate solid residue (i.e. the solid residue isolated from the screening experiment with malic acid) showed a pattern similar to Compound A, as shown in FIG. 28. In yet further embodiments, a malate salt of Compound A is provided. In some aspects, the malate salt of Compound A is in a crystalline form. A crystalline malate solid residue of Compound A may be characterized by an XRPD pattern comprising peaks at 6.3, 12.6, 17.0, and 18.8 degrees two theta±0.2 degrees two theta. The XRPD of a crystalline malate salt of Compound A may further comprise one or more of the following peaks: 14.0, 23.0, or 25.2 degrees two theta±0.2 degrees two theta. A crystalline malate salt of Compound A may further be characterized by an XRPD pattern substantially as depicted in FIG. 28. The DSC thermogram of the malate solid residue exhibited an endothermic event with a peak temperature at about 195° C. as depicted in FIG. 37. The malate solid residue a solution $^1$H-NMR spectrum as shown in FIG. 19. The malate solid residue of Compound A may further be characterized by an X-ray powder diffraction pattern comprising those peaks identified in Table 8, wherein the relative intensity of the peaks is greater than about 2%, more preferably greater than about 5%, more preferably greater than about 10%.

In treatment methods according to the disclosure, an effective amount of a compound according to the disclosure is administered to a subject suffering from or diagnosed as having such a disease, disorder, or condition. An "effective amount" means an amount or dose sufficient to generally bring about the desired therapeutic benefit in patients in need of such treatment for the designated disease, disorder, or condition. Effective amounts or doses of the compounds of the present disclosure may be ascertained by routine methods such as modeling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day.

In addition, the compounds may be used in combination with additional active ingredients in the treatment of the above conditions. The additional active ingredients may be coadministered separately with a compound of the disclosure or included in a pharmaceutical composition according to the disclosure. The combination may serve to increase efficacy (e.g., by including in the combination a compound potentiating the potency or effectiveness of a compound), decrease one or more side effects, or decrease the required dose of the compound.

The compounds are used, alone or in combination with one or more additional active ingredients, to formulate pharmaceutical compositions of the disclosure. A pharmaceutical composition of the disclosure comprises: (a) an effective amount of at least one compound in accordance with the disclosure; and (b) a pharmaceutically acceptable excipient.

Delivery forms of the pharmaceutical compositions containing one or more dosage units of compounds may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation. The route of delivery includes immediate release, timed release and sustained release.

The preparation may be in the form of tablets, caplets, gelcaps, capsules, drops, sachets, dragees, powders, granules, lozenges, powders for reconstitution, liquid preparations, or suppositories. In some embodiments, the compositions are formulated for intravenous infusion, topical administration, or oral administration.

For oral administration, the compounds of the disclosure can be provided in the form of tablets or capsules, or as a solution, elixir, emulsion, or suspension. The total daily dosage of about 5 mg to 5 g daily, preferably about 10 mg to about 1000 mg daily, more preferably about 50 mg to about 500 mg daily, may be accomplished by dosing once, twice, three, or four times per day.

Oral tablets may include one or more of a compound according to the disclosure mixed with pharmaceutically acceptable excipients such as inert diluents, disintegrating agents, binding agents, lubricating agents, sweetening agents, flavoring agents, coloring agents, suspending agents, dyes and preservative agents. Suitable inert fillers include sodium and calcium carbonate, sodium and calcium phosphate, lactose, starch, sugar, glucose, methyl cellulose, magnesium stearate, mannitol, sorbitol, and the like. Liquid oral excipients may include ethanol, glycerol, water, and the like. Starch, polyvinyl-pyrrolidone, sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, compounds of the disclosure may be mixed with a solid, semisolid, or liquid diluent. Soft gelatin capsules may be prepared by mixing the compound of the disclosure with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain pharmaceutically acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compounds may also be administered by non-oral routes. For example, the compositions may be formulated for rectal administration as a suppository. For parenteral use, including intravenous, intramuscular, intraperitoneal, or subcutaneous routes, the compounds of the disclosure may be provided in sterile aqueous solutions or suspensions, buffered to an appropriate pH and isotonicity or in parenterally acceptable oil. Suitable aqueous vehicles include Ringer's solution and isotonic sodium chloride. Such forms will be presented in unit-dose form such as ampules, auto-injectors, or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of compound, admixed with a pharmaceutical carrier over a period ranging from several minutes to several days. Other routes of administration include, without limitation, intracerebral, intraventricular, intracerebroventricular, intrathecal, intracisternal, intraspinal and/or peri-spinal routes.

For topical administration, the compounds may be mixed with a pharmaceutical carrier at a concentration of about 0.1% to about 10% of drug to vehicle. Another mode of administering the compounds of the disclosure may utilize a patch formulation to affect transdermal delivery.

Compounds of the disclosure may alternatively be administered in methods of this disclosure by inhalation, via the nasal or oral routes, e.g., in a spray formulation also containing a suitable carrier such as an aerosol or liquid spray.

The sulfate salt, phosphate salt, mesylate salt, tosylate salt and besylate salt of Compound A alone, in combination with each other, or in combination with Compound A are accordingly useful in inhibiting colony-stimulating factor-1 receptor. In some embodiments, the sulfate salt, phosphate salt, mesylate salt, tosylate salt and besylate salt of Compound A are useful in methods of treating a disease that is at least one of osteoporosis, Paget's disease, rheumatoid arthritis and other forms of inflammatory arthritis, osteoarthritis, prosthesis failure, osteolytic sarcoma, myeloma, or tumor metastasis to bone. In some embodiments, the disease is rheumatoid arthritis or cancer such as cancer metastasis to bone. In other embodiments, the sulfate salt, phosphate salt, mesylate salt, tosylate salt and besylate salt of Compound A are useful in treating a disease that is glomerulonephritis, inflammatory bowel disease, sarcoidosis, congestive obstructive pulmonary disease, idiopathic pulmonary fibrosis, asthma, pancreatitis, HIV infection, psoriasis, diabetes, tumor-related angiogenesis, age-related macular degeneration, diabetic retinopathy, restenosis, schizophrenia, or Alzheimer's dementia. In further embodiments, the sulfate salt, phosphate salt, mesylate salt, tosylate salt and besylate salt of Compound A is useful in treating pain, including skeletal pain caused by tumor metastasis or osteoarthritis, or visceral, inflammatory, or neurogenic pain. In still other embodiments, the sulfate salt, phosphate salt, mesylate salt, tosylate salt and besylate salt of Compound A is useful in treating a disease that is ovarian cancer, uterine cancer, breast cancer, prostate cancer, lung cancer, colon cancer, stomach cancer, or hairy cell leukemia. In yet further embodiments, the sulfate salt, phosphate salt, mesylate salt, tosylate salt and besylate salt of Compound A is useful in treating or preventing metastasis from ovarian cancer, uterine cancer, breast cancer, prostate cancer, lung cancer, colon cancer, stomach cancer, or hairy cell leukemia. In other embodiments, the sulfate salt, phosphate salt, mesylate salt, tosylate salt and, besylate salt of Compound A is useful in treating an autoimmune disease that is at least one of systemic lupus erythematosus, rheumatoid arthritis and other forms of inflammatory arthritis, psoriasis, Sjogren's syndrome, multiple sclerosis, or uveitis.

The following Examples are set forth to aid in the understanding of the invention, and are not intended and should not be construed to limit in any way the invention set forth in the claims which follow thereafter.

EXAMPLES

Example 1: Synthesis of Compound A

The hydrochloride salt of Compound A was prepared as described in U.S. Pat. No. 8,497,376. Water (150 mL) was added to the hydrochloride salt of Compound A (about 10 g). The formed solution was stirred using a stir plate. After several days, the solution was filtered using a Buchner glass filter under vacuum until the majority of the water was removed. A flow of $N_2$ gas was then applied onto the surface of the precipitate for about 1 hour to ensure complete removal of the solvent. The glass filter was weighed before and after the filtration and the net weight was recorded.

Figure 3:
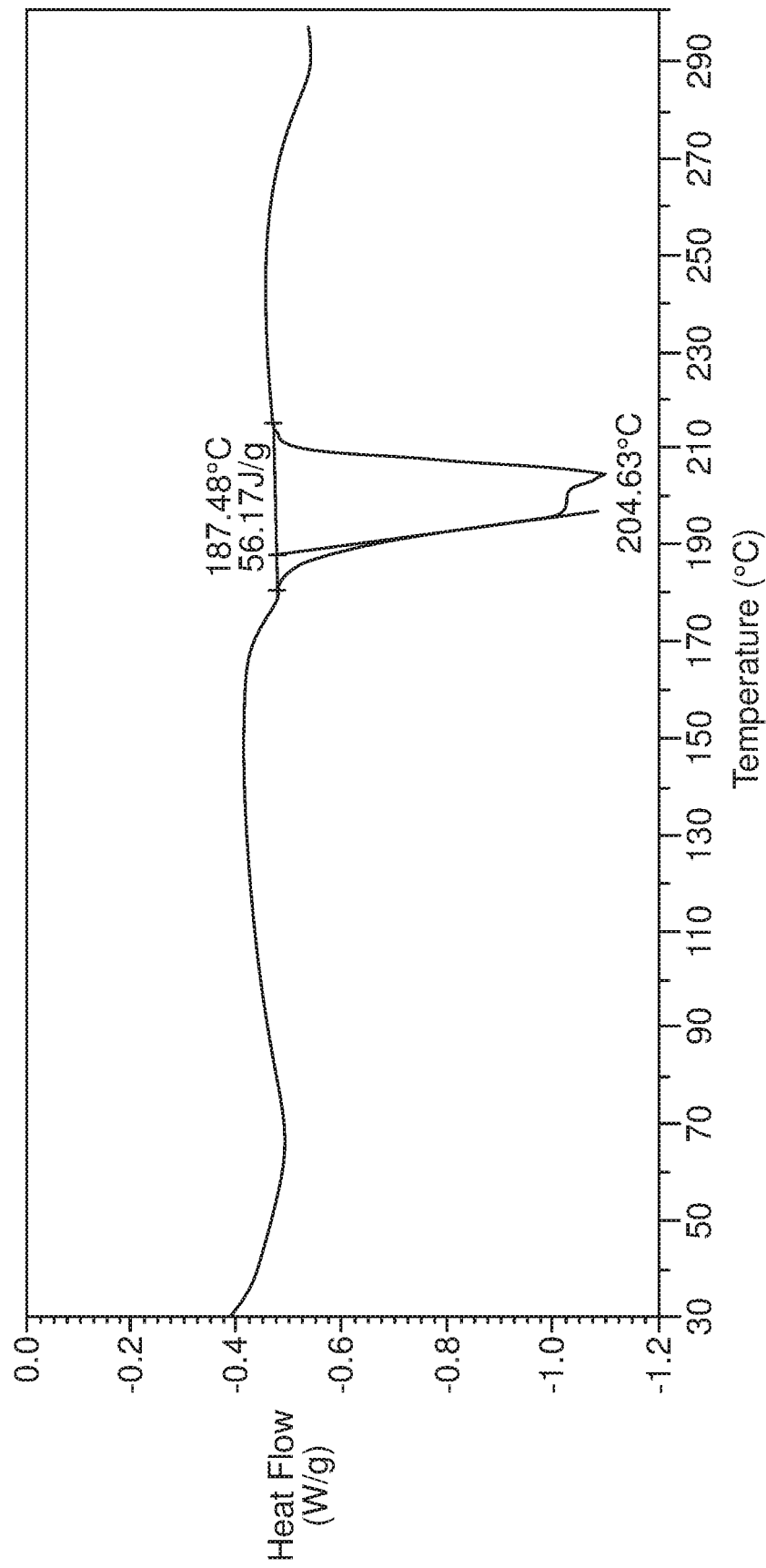
FIG. 3 is a differential scanning calorimetry (DSC) thermogram of Compound A.
Figure 4:
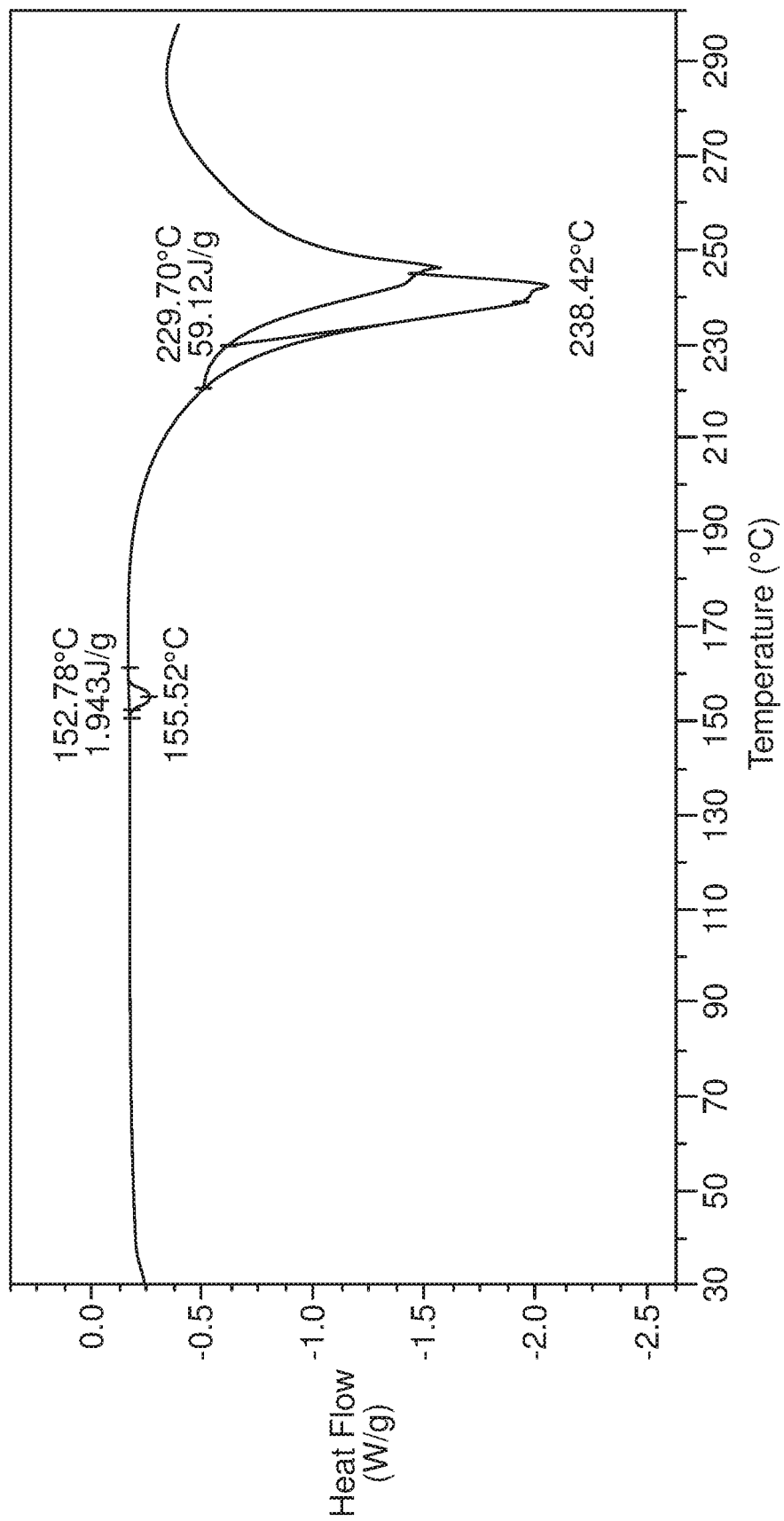
FIG. 4 is a DSC thermogram for the HCl salt of Compound A.
Figure 5:
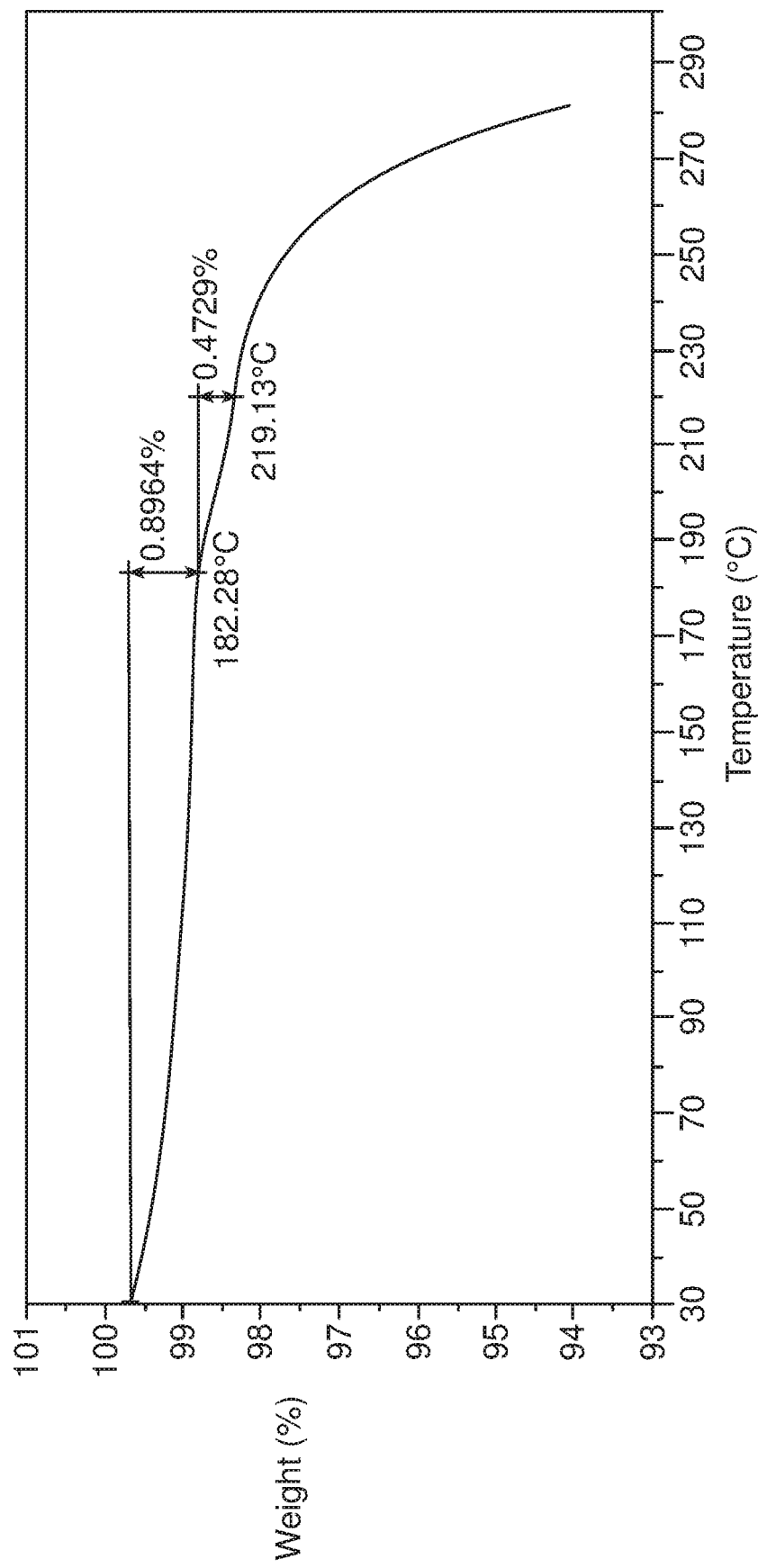
FIG. 5 is a thermogravimetric analysis (TGA) spectrum of Compound A.
Figure 6:
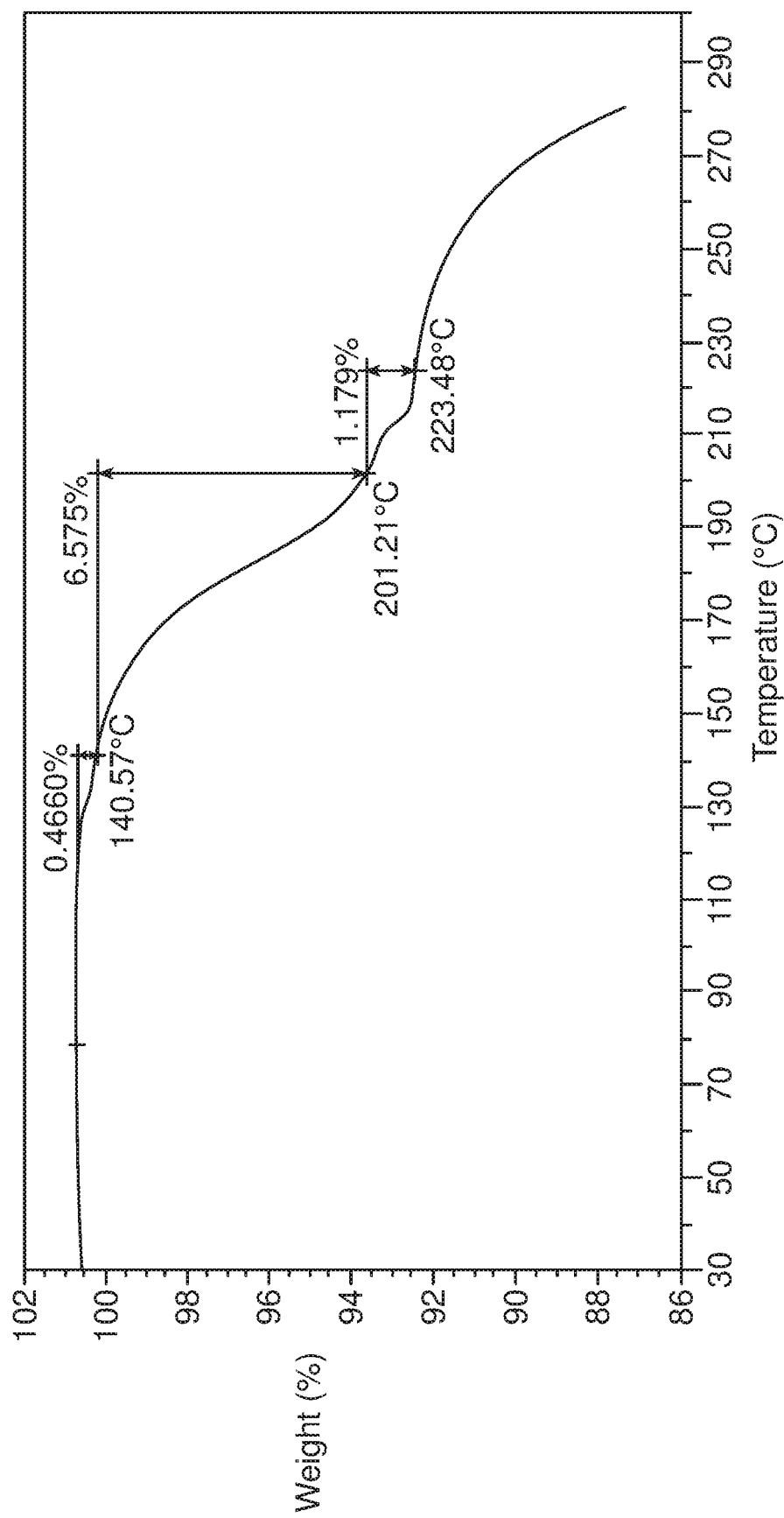
FIG. 6 is a TGA spectrum of the HCl salt of Compound A.
Figure 7:
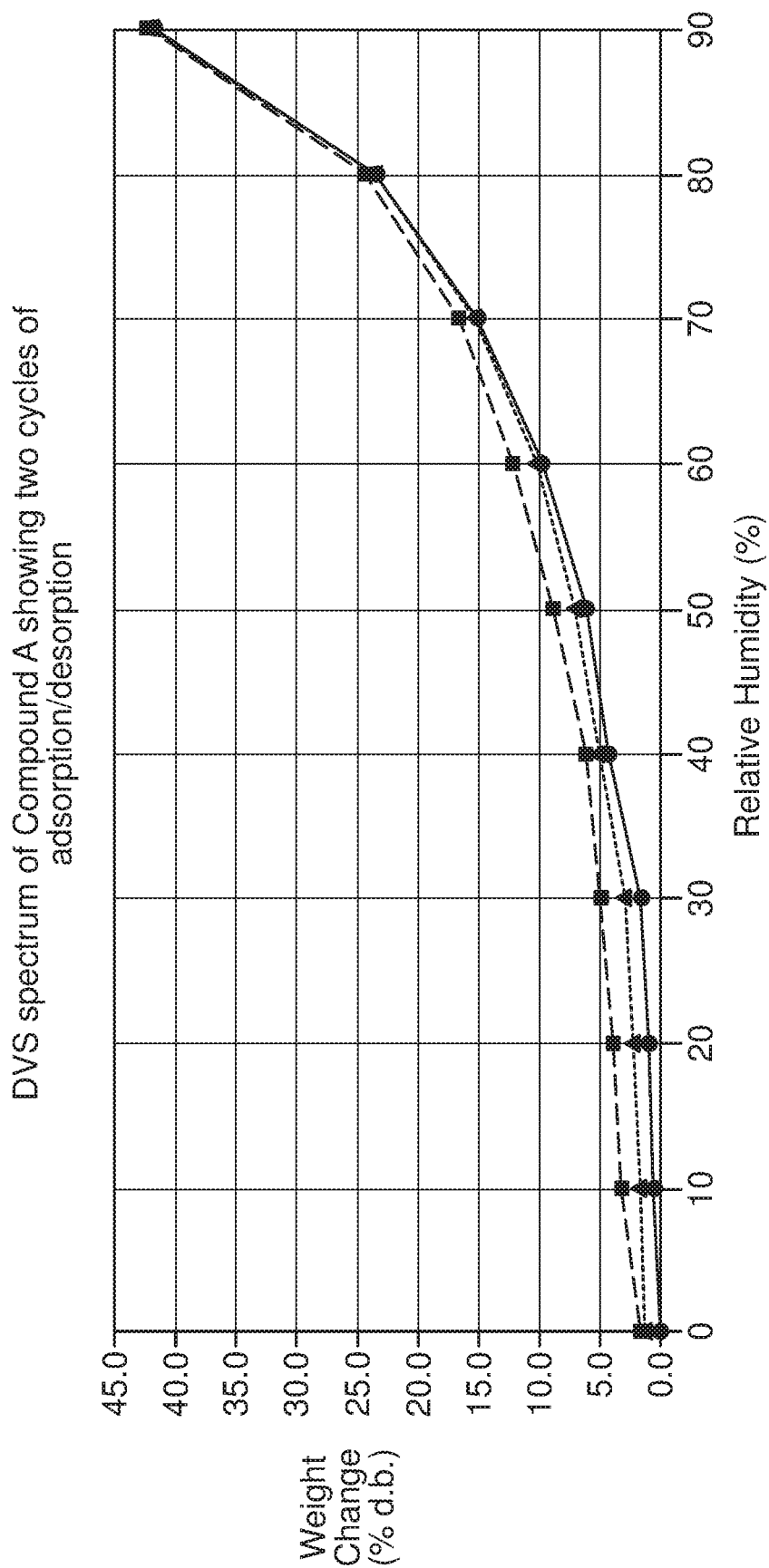
FIG. 7 is a dynamic vapor sorption (DVS) spectrum of Compound A showing two cycles of adsorption/desorption.

A portion of the precipitate was analyzed using XRD and the results confirmed the conversion of the salt to the free base, Compound A. The glass filter was placed in a vacuum oven at 60° C. overnight to ensure complete dryness until a constant weight was obtained. Final examination of the solids by XRD (e.g., FIG. 1), by comparison of the XRD of the isolated solids with the XRD of a sample of the HCl salt of Compound A (e.g., FIG. 2), confirmed the formation of the free base, Compound A. DSC (e.g., FIGS. 3 and 4) and TGA (e.g., FIGS. 5 and 6) analysis of Compound A and the HCl salt provided further evidence of the formation of Compound A from the HCl salt.

Example 2: Synthesis of Compound A Salts

The salts and solid residues of Compound A were prepared using nine different acidic counter-ions, (wherein the acidic counter-ion is provided by the corresponding acid i.e., sulfuric, phosphoric, methanesulfonic, p-toluenesulfonic, benzenesulfonic, malonic, citric, 1-malic, and acetic acids), using the following synthetic procedure.

Nine samples of Compound A (about 20 mg) prepared as described in Example 1 were added to nine separate 4 mL vials. About 1.1 molar equivalents of the acid (i.e., sulfuric acid, phosphoric acid, methanesulfonic acid, p-toluenesulfonic acid, benzenesulfonic acid, malonic acid, citric acid, 1-malic acid, and acetic acid) solutions (0.1 M in acetone, freshly prepared) was independently added to each vial. The vials were stirred at 500 rpm and heat was applied as necessary. All solutions formed suspensions upon addition of the acid solution to Compound A, with the exception that the acetic acid solution remained a clear mixture. The suspensions were then heated to 40° C. with stirring for about 30 minutes, but no additional clear solutions were observed. Since the solubility of Compound A in acetone is about 130 mg/mL, the formation of a suspension was interpreted as an indication that a salt or other non-free base material (e.g. solvate, co-crystal, etc.) had formed.

All solutions were allowed to slowly crystallize by keeping the vials capped for 24 hours, and then uncapping the vials and allowing evaporation to total dryness. All residual solids were then analyzed using solution $^1$H-NMR, XRPD, DSC and TGA as described below.

Example 3: XRPD Analysis

X-ray powder diffraction (XRPD) was performed using an X-ray diffractometer (Philips Model X'Pert PRO PW3040) equipped with X'Celerator detector and graded multilayer parabolic X-ray mirror. The sample was scanned from 3 to 400 two theta at a step size of 0.0165° two theta and a time per step of 48.260 seconds. The x-ray tube voltage and current settings were 45 KV and 40 mA, respectively. The sample was packed on a zero background holder and scanned under ambient conditions of temperature and humidity. One skilled in the art will recognize that diffraction patterns and peak positions are typically independent of the diffractometer used and whether a specific calibration method was utilized. Typically, the peak positions may vary by about ±0.2° two theta, or less. The intensities (and relative intensities) of each specific diffraction peak may also vary as a function of various factors, including but not limited to particle size, orientation, sample purity, etc. However the skilled person will be able to differentiate between the prepared forms including the sulfate salt, phosphate salt, mesylate salt, tosylate salt, besylate salt, acetate solid residue, malonate solid residue, citrate solid residue and malate solid residue of Compound A.

Figure 2:
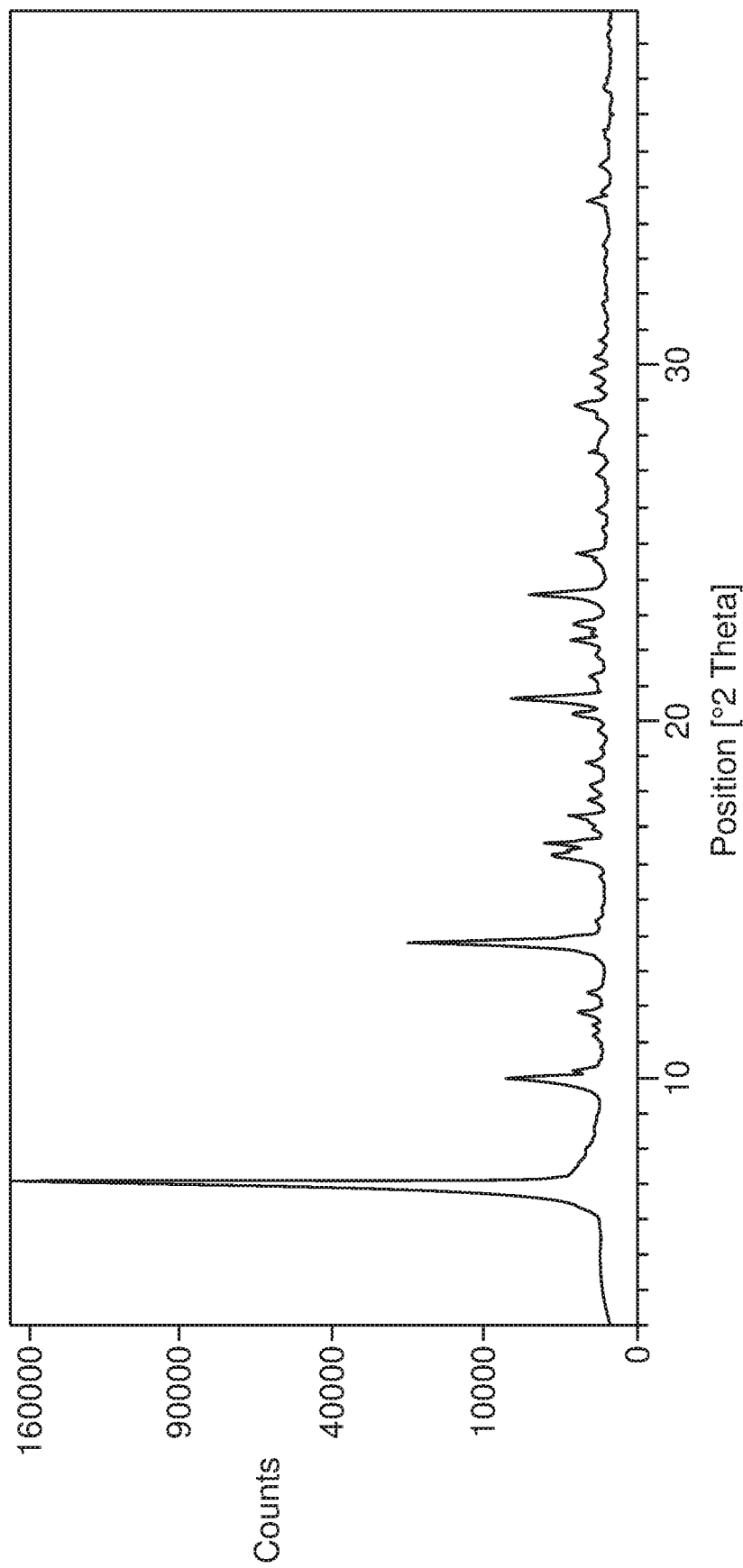
FIG. 2 is an XRPD pattern for the HCl salt of Compound A.

XRPD patterns of Compound A (prepared as described in Example 1 above) and the HCl salt of Compound A were obtained (see, FIGS. 1 and 2). Small portions of each of the different suspensions from Example 1 were withdrawn, prior to total evaporation, and placed to dry on a zero background X-ray sample holder for analysis. XRPD analyses of the residues isolated from aliquots withdrawn from the suspensions showed diffraction patterns which indicated that a form other than the Compound A freebase was formed, indicating possible salt formation.

XRPD patterns of the solid residues isolated from the phosphate, mesylate, tosylate, and besylate solutions showed crystalline patterns that were different than Compound A, indicating salt formations. The XRPD pattern of the solid residue isolated from the sulfate solution was featureless indicating an amorphous solid (see, FIG. 20).

Table 1 provides the peak listings for the XRPD of the phosphate salt (see, also, FIG. 21).

TABLE 1

| Position [°2θ] | Relative Intensity [%] |
| --- | --- |
| 6.3 | 25.4 |
| 6.7 | 100.0 |
| 17.0 | 2.3 |
| 17.7 | 2.1 |
| 20.0 | 6.3 |

Table 2 provides the peak listings for the XRPD of the mesylate salt (see, also, FIG. 22).

TABLE 2

| Position [°2θ] | Relative Intensity [%] |
| --- | --- |
| 5.0 | 9.5 |
| 6.0 | 100.0 |
| 6.3 | 6.9 |
| 8.1 | 43.2 |
| 12.1 | 3.3 |
| 13.5 | 2.2 |
| 16.3 | 2.7 |
| 17.6 | 2.8 |
| 18.1 | 31.1 |
| 18.9 | 4.8 |
| 19.7 | 3.4 |
| 20.8 | 2.3 |
| 24.3 | 9.5 |
| 24.7 | 2.2 |

Table 3 provides the peak listings for the XRPD of the tosylate salt (see, also, FIG. 23).

TABLE 3

| Position [°2θ] | Relative Intensity [%] |
| --- | --- |
| 5.1 | 100.0 |
| 5.8 | 27.7 |
| 5.9 | 24.5 |
| 6.4 | 71.6 |
| 6.5 | 56.8 |
| 11.9 | 5.6 |
| 14.9 | 4.9 |
| 15.4 | 8.1 |
| 16.3 | 11.3 |
| 17.2 | 15.2 |
| 18.5 | 7.4 |
| 19.6 | 10.2 |
| 22.5 | 4.1 |
| 25.0 | 6.5 |
| 27.0 | 3.8 |
| 29.9 | 2.0 |

Table 4 provides the peak listings for the XRPD of the besylate salt (see, also, FIG. 24).

TABLE 4

| Position [°2θ] | Relative Intensity [%] |
| --- | --- |
| 5.8 | 86.0 |
| 6.3 | 100.0 |
| 7.4 | 4.2 |
| 7.8 | 16.9 |
| 8.6 | 17.6 |
| 8.9 | 18.8 |
| 11.6 | 8.7 |
| 12.4 | 3.2 |
| 12.6 | 6.3 |
| 12.7 | 4.1 |
| 14.1 | 5.1 |
| 14.4 | 2.9 |
| 14.7 | 5.0 |
| 15.0 | 2.1 |

TABLE 4-continued

| Position [°2θ] | Relative Intensity [%] |
|---|---|
| 15.5 | 8.6 |
| 16.1 | 2.6 |
| 17.1 | 21.0 |
| 17.4 | 33.4 |
| 17.6 | 20.9 |
| 18.2 | 14.5 |
| 18.9 | 10.3 |
| 19.2 | 3.4 |
| 19.6 | 12.0 |
| 20.2 | 3.0 |
| 21.9 | 5.0 |
| 22.4 | 2.3 |
| 23.0 | 10.7 |
| 23.9 | 7.6 |
| 24.6 | 2.8 |
| 25.0 | 3.6 |
| 25.3 | 4.2 |

Table 5 provides the peak listings for the XRPD of the acetate solid residue (see, also, FIG. 25).

TABLE 5

| Position [°2θ] | Relative Intensity [%] |
|---|---|
| 6.1 | 100.0 |
| 6.3 | 17.3 |
| 9.2 | 35.1 |
| 9.4 | 6.1 |
| 12.7 | 18.6 |
| 14.6 | 4.9 |
| 15.1 | 31.8 |
| 18.4 | 19.9 |
| 21.1 | 4.0 |
| 22.2 | 2.3 |
| 24.8 | 2.1 |
| 26.3 | 3.7 |

Table 6 provides the peak listings for the XRPD of the malonate solid residue (see, also, FIG. 26).

TABLE 6

| Position [°2θ] | Relative Intensity [%] |
|---|---|
| 6.3 | 100.0 |
| 6.9 | 17.9 |
| 7.4 | 6.0 |
| 10.7 | 3.0 |
| 11.5 | 2.7 |
| 12.2 | 2.2 |
| 12.5 | 5.8 |
| 14.0 | 3.0 |
| 14.8 | 4.4 |
| 15.5 | 4.0 |
| 17.0 | 9.6 |
| 17.3 | 4.2 |
| 18.3 | 4.1 |
| 18.6 | 3.6 |
| 18.8 | 5.1 |
| 20.0 | 2.3 |
| 20.2 | 2.3 |
| 23.0 | 5.0 |
| 23.6 | 3.1 |
| 25.2 | 2.0 |

Table 7 provides the peak listings for the XRPD of the citrate solid residue (see, also, FIG. 27).

TABLE 7

| Position [°2θ] | Relative Intensity [%] |
|---|---|
| 6.3 | 100.0 |
| 12.5 | 4.5 |
| 14.0 | 3.5 |
| 17.0 | 5.1 |
| 18.8 | 5.8 |
| 23.0 | 2.6 |

Table 8 provides the peak listings for the XRPD of the malate solid residue (see, also, FIG. 28).

TABLE 8

| Position [°2θ] | Relative Intensity [%] |
|---|---|
| 6.3 | 100.0 |
| 12.6 | 5.6 |
| 14.0 | 4.1 |
| 17.0 | 7.5 |
| 18.8 | 8.7 |
| 23.0 | 5.0 |
| 25.2 | 2.9 |

Example 4: Solution $^1$H-NMR Analysis

Figure 10:
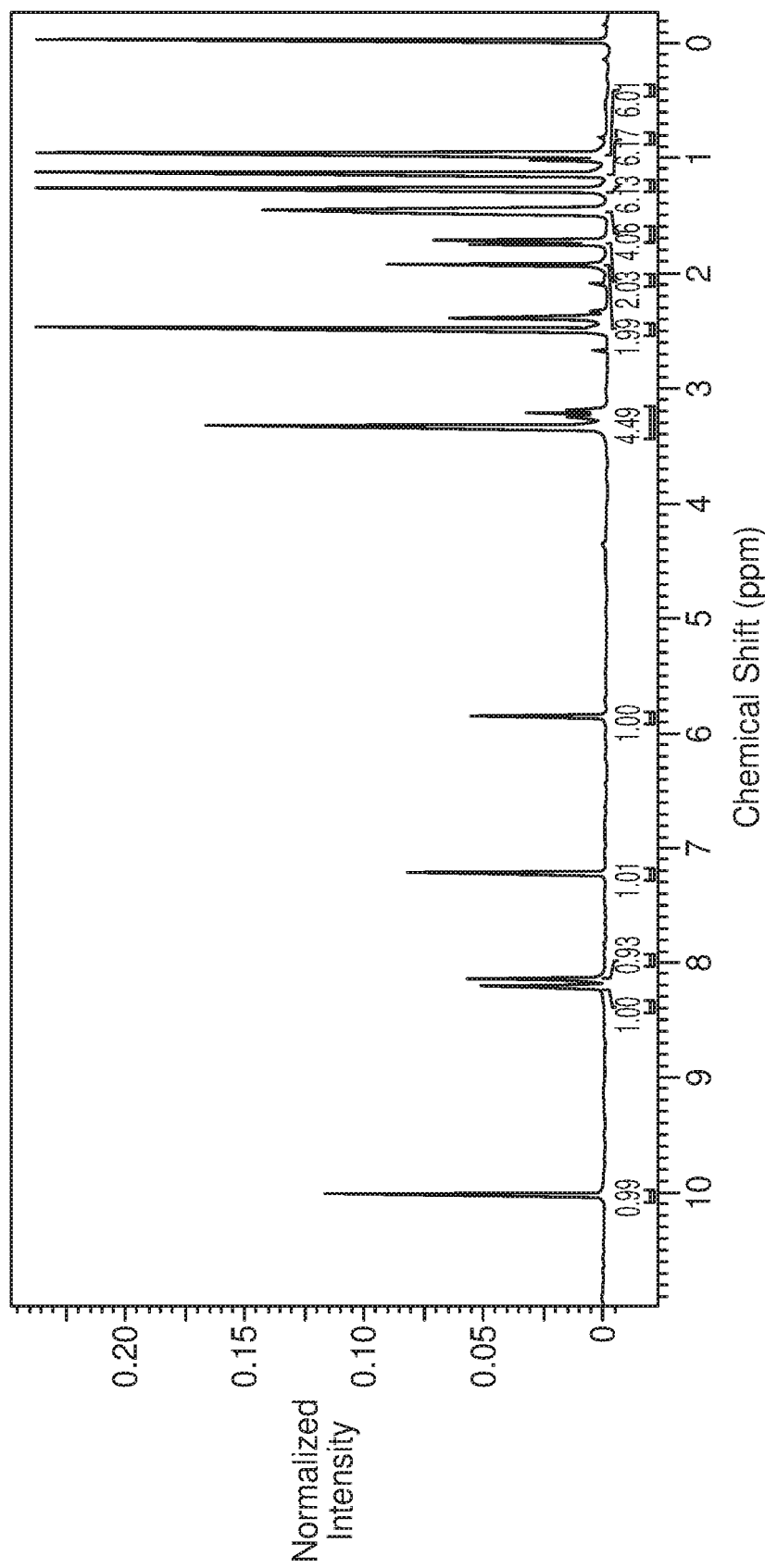
FIG. 10 is a solution proton nuclear magnetic resonance ($^1$H-NMR) spectrum of Compound A.

Solution $^1$H-NMR analysis of Compound A was conducted and used as a reference (see, FIG. 10). Solution $^1$H-NMR patterns were then obtained from the residues obtained in Example 1 (see, FIG. 11 (sulfate salt), FIG. 12 (phosphate salt), FIG. 13 (mesylate salt), FIG. 14 (tosylate salt), FIG. 15 (besylate salt), FIG. 16 (acetate solid residue), FIG. 17 (malonate solid residue), FIG. 18 (citrate solid residue), and FIG. 19 (malate solid residue). The residues from the salt solutions showed chemical shifts of the protons at one or both of the 7.2 and 8.2 ppm peaks attributable to the hydrogen atoms in the pyridine ring portion of Compound A, indicating the possible formation of salts of Compound A.

Example 5: Thermal Analysis

Thermal analyses were performed using a TA instrument Model Q1000 DSC. The sample was run in an open aluminum pan. The reference used was an empty aluminum pan. The sample was scanned from 25° to 300° C. with a programmed heating rate of 10° C./min. Total weight loss of the sample was obtained using a TA instrument Model Q5000 TGA. The sample was placed in a tarred aluminum pan, automatically weighed, and inserted into the TGA furnace. The sample was scanned from 25° to 300° C. at a heating rate of 10° C./min with a 25 mL/min nitrogen sample purge and a 10 mL/min nitrogen balance purge.

Differential scanning calorimetry and thermogravimetric analyses were conducted on Compound A prepared as described in Example 1 above (see, FIGS. 3 and 5), the HCl salt of Compound A (see, FIGS. 4 and 6) and the residues obtained in Example 2 (see, FIGS. 29-37).

The DSC thermogram of the sulfate salt (see FIG. 29) showed three endothermic events with peak temperatures at 47.4° C. (61.0 J/g heat of fusion), 207.2° C. (8.93 J/g heat of fusion), and 232.8° C. (2.06 J/g heat of fusion), respectively. TGA of the sulfate salt showed a two-step weight loss of 2.3% between room temperature and 109° C. due to possible dehydration/desolvation, and 7.9% between 109° C. and 243° C. due to melting/decomposition.

DSC analysis of the phosphate salt (see FIG. 30) showed two endothermic events with peak temperatures at 192.3° C. (4.7 J/g heat of fusion), and 222.2° C. (55.7 J/g heat of fusion), respectively. TGA of the phosphate salt showed a two-step eight loss of 1.7% between room temperature and 203° C. due to possible dehydration/desolvation, and 1.7% between 203° and 240° C. due to melting/decomposition.

DSC of the mesylate salt (see FIG. 31) showed one endothermic event due to melting with a peak temperature at 256.3° C. (205.2 J/g heat of fusion). TGA of the mesylate salt showed a two-step weight loss of 1.1% between room temperature and 222° C. due to possible dehydration/desolvation, and 5.7% between 222° C. and 264° C. due to melting/decomposition.

DSC of the tosylate salt (see FIG. 32) showed two endothermic events with peak temperatures at 155.9° C. (2.2 J/g heat of fusion), 207.4° C. (31.5 J/g heat of fusion) and 255.9° C. (2.9 J/g heat of fusion), respectively. TGA of the tosylate salt showed a two-step weight loss of 2.7% between room temperature and 168° C. due to possible dehydration/desolvation, and 3.4% between 168° C. and 244° C. due to melting/decomposition.

DSC of the besylate salt (see FIG. 33) showed three endothermic events with peak temperatures at 51.5° C. (39.1 J/g heat of fusion), 164.8° C. (11.1 J/g heat of fusion), and 212.2° C. (21.0 J/g heat of fusion), respectively. TGA of the besylate salt showed a three-step weight loss of 1.7% between room temperature and 76° C. due to possible dehydration/desolvation, 0.6% between 76° C. and 183° C., and 3.5% between 183° C. and 256° C. due to melting/decomposition.

DSC of the acetate solid residue (see FIG. 34) showed one endothermic event due to melting with a peak temperature at 210.9° C. (45.8 J/g heat of fusion). TGA of the acetate solid residue showed a two-step weight loss of 0.3% between room temperature and 157° C. due to possible dehydration/desolvation, and 3.9% between 157° C. and 232° C. due to melting/decomposition.

DSC of the malonate solid residue (see FIG. 35) showed three endothermic events with peak temperatures at 174.6° C. (117.4 J/g heat of fusion), 210.3° C. (6.8 J/g heat of fusion), and 220.7° C. (37.2 J/g heat of fusion), respectively. TGA of the malonate solid residue showed a one-step weight loss of 16.8% between 128° C. and 189° C. due to melting/decomposition.

DSC of the citrate solid residue (see FIG. 36) showed three endothermic events with peak temperatures at 134.3° C. (6.1 J/g heat of fusion), 212.6° C. (23.1 J/g heat of fusion), and 221.5° C. (9.61 J/g heat of fusion), respectively. TGA of the citrate solid residue showed a two-step weight loss of 0.5% between room temperature and 120° C. due to possible dehydration/desolvation, and 21.9% between 120° C. and 194° C. due to melting/decomposition.

DSC of the malate solid residue (see FIG. 37) showed one endothermic event due to melting with a peak temperature at 195° C. (108.3 J/g heat of fusion). TGA of the malate solid residue showed a two-step weight loss of 0.9% between room temperature and 146° C. due to possible dehydration/desolvation, and 16.3% between 146° C. and 237° C. due to melting/decomposition.

Example 6: Moisture Sorption Analysis

The moisture sorption analysis was performed using a Hiden Isochema system Model IGAsorp. The sample was run in a stainless-steel mesh crucible. The sample was initially dried at 60° C. for 30 minutes then the moisture profile was evaluated by monitoring vapor adsorption/desorption over the range of 0 to 90% relative humidity at 25° C. The moisture profile consisted of 2 cycles of vapor adsorption/desorption.

Figure 8:
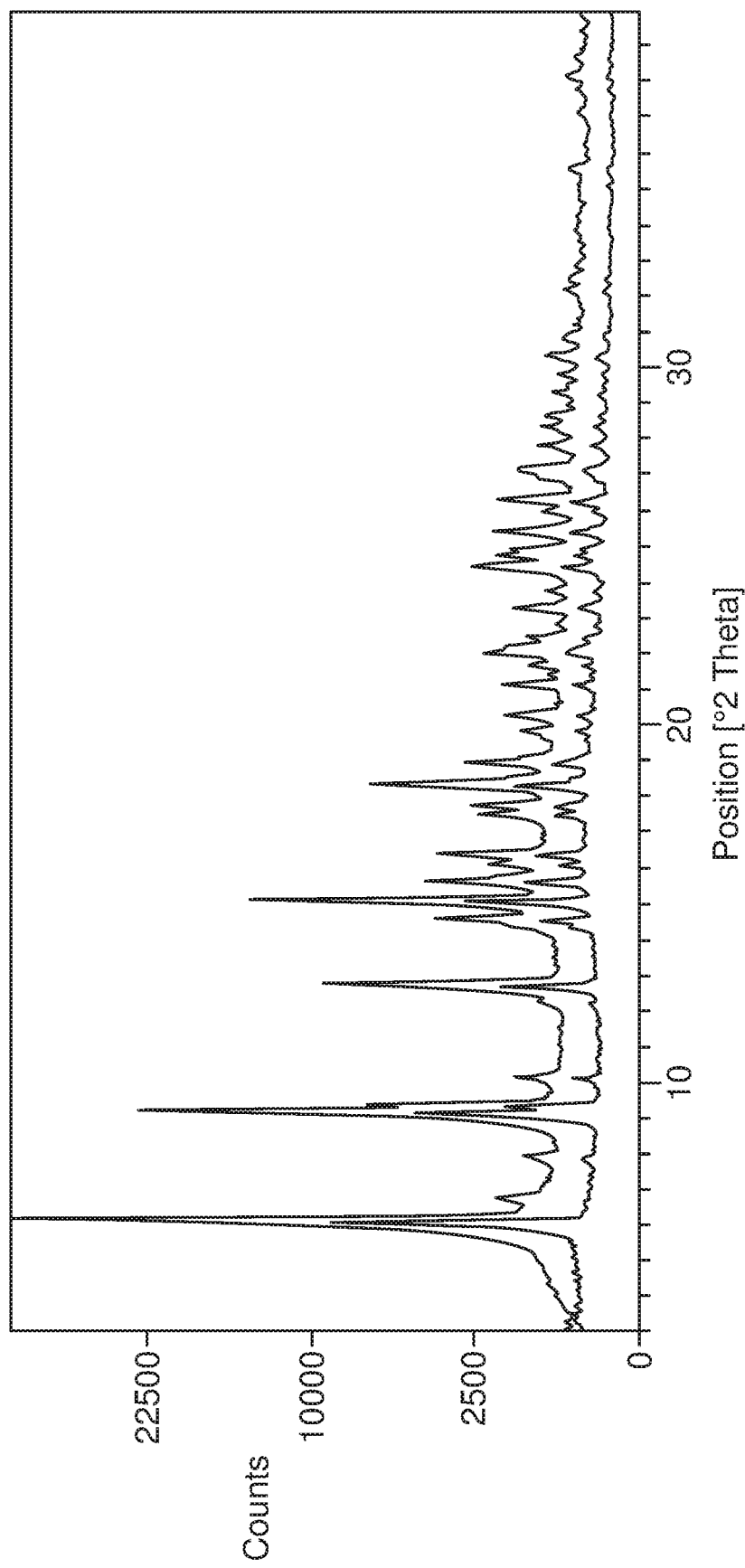
FIG. 8 is the XRPD pattern of Compound A before (bottom) and after (top) DVS.
Figure 9:
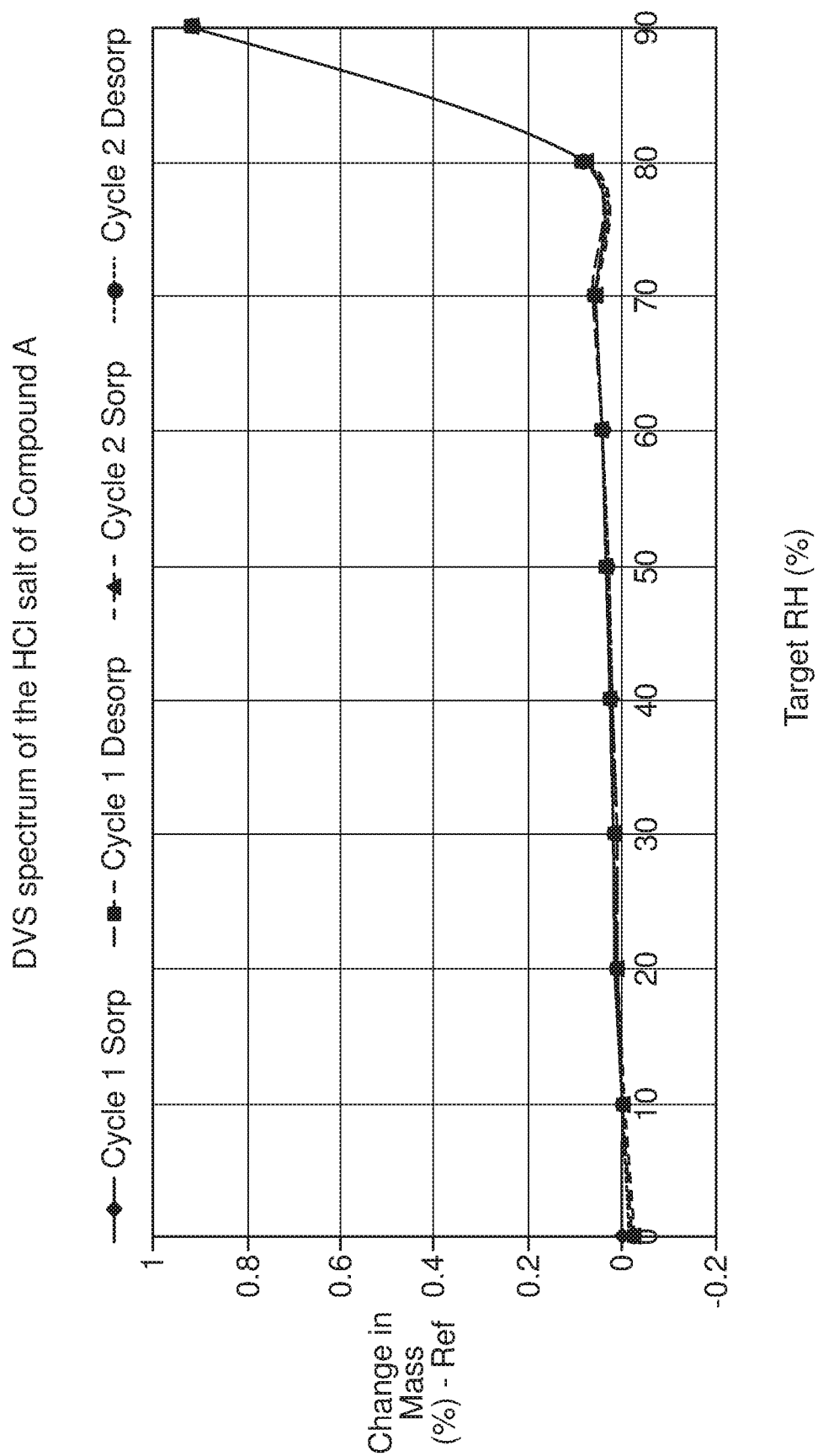
FIG. 9 is the DVS spectrum of the HCl salt of Compound A.
Figure 39:
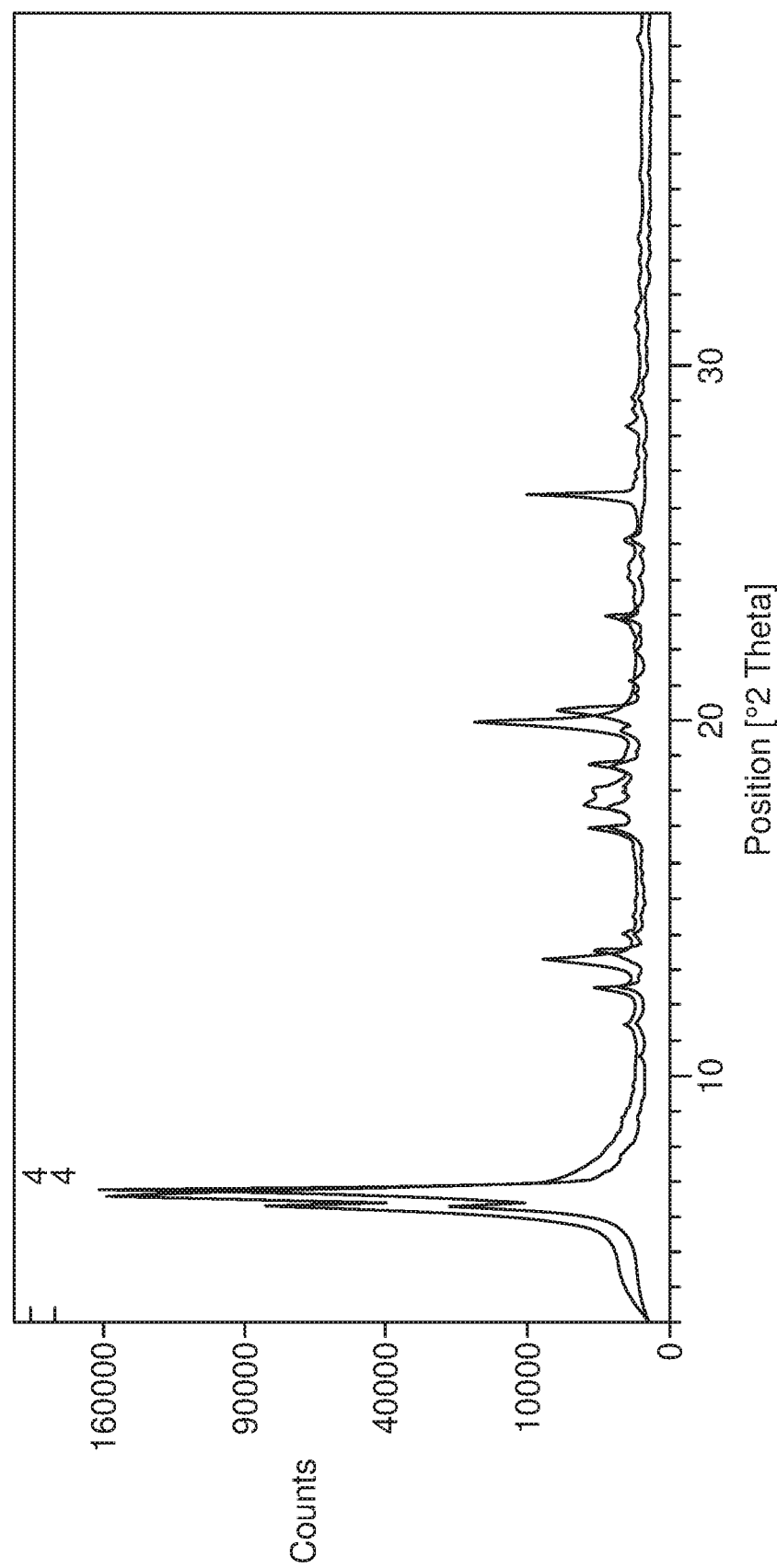
FIG. 39 are XRPD patterns of the phosphate salt of Compound A before (top/upper spectrum) and after DVS (bottom/lower spectrum).
Figure 40:
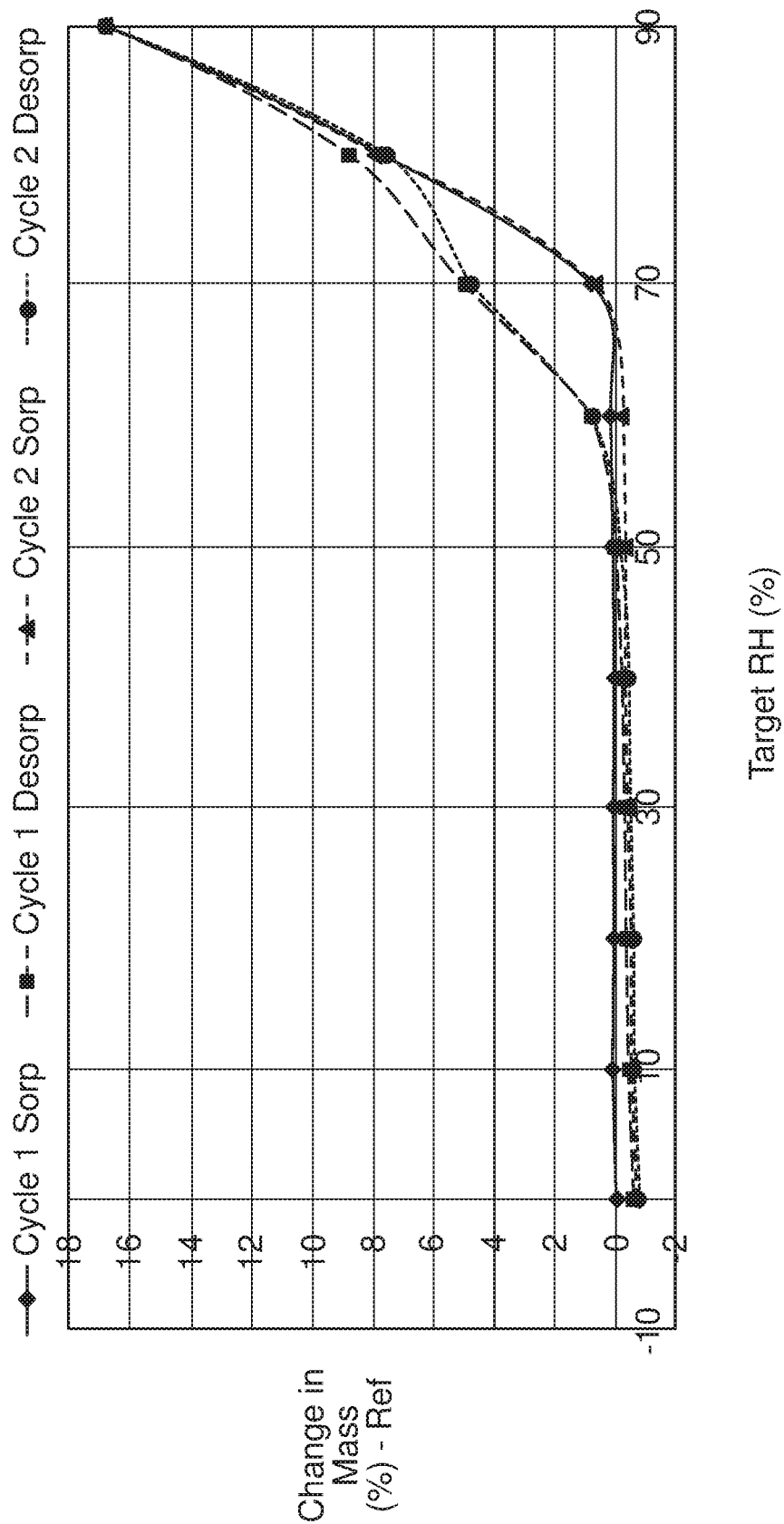
FIG. 40 is a DVS spectrum of the mesylate salt of Compound A showing two cycles of adsorption.
Figure 41:
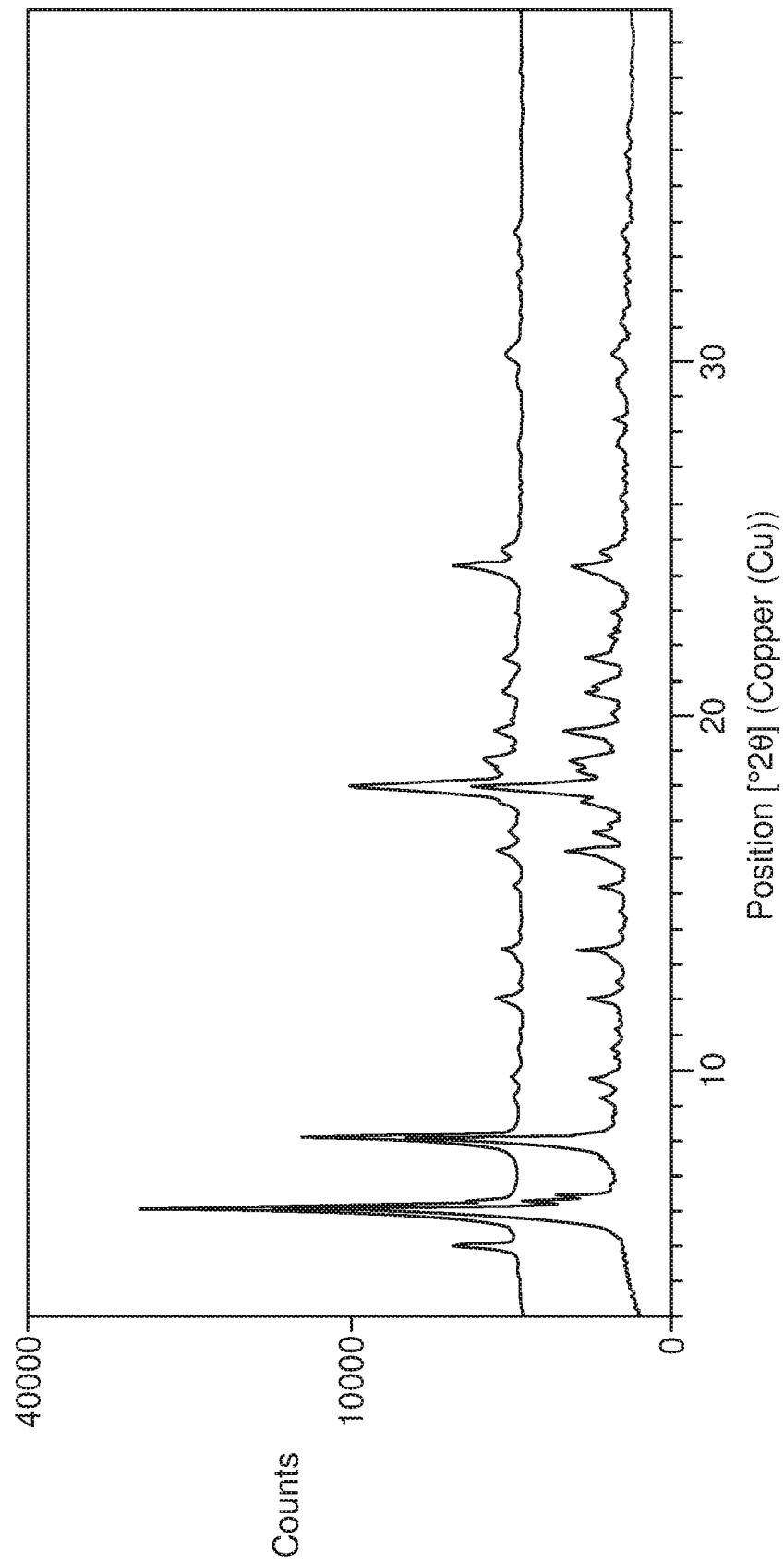
FIG. 41 are XRPD patterns of the mesylate salt of Compound A before (top/upper spectrum) and after DVS (bottom/lower spectrum).

Dynamic vapor sorption was performed on Compound A (prepared as described in example 1 above), the HCl salt of Compound A, phosphate salt of Compound A, and mesylate salt of Compound A and the moisture sorption spectra obtained (see, FIGS. 7, 9, 38, and 40, respectively). Following DVS, the samples of Compound A, phosphate salt of Compound A and mesylate salt of Compound A were subjected to XRPD (see, FIGS. 8, 39, and 41, respectively).

DVS of the phosphate salt (see FIG. 38) showed that it was hygroscopic with moisture adsorption of 13% up to 90% relative humidity. No hysteresis was observed and it retained 0.6% moisture at the end of the second cycle. XRPD of the solid residues remaining after DVS showed no change in the crystalline form.

DVS of the mesylate salt showed that it was hygroscopic with moisture adsorption of 0.2% up to 60% relative humidity and a total of 17% up to 90% relative humidity. Very little hysteresis was observed and it retained 0.2% moisture at the end of the second cycle while there is a strong hysteresis between 80%-60% relative humidity during the desorption cycle. XRPD analysis of the solid residue remaining after DVS of the mesylate salt was unchanged relative to the XRPD of a sample of the mesylate salt measured before DVS (see FIG. 41, where the top/upper spectrum represents the XRPD of a sample of the mesylate salt before DVS, and the bottom/lower spectrum represents the XRPD of a sample of the mesylate salt after DVS).

The disclosures of each patent, patent application, and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A pharmaceutically acceptable salt form of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide (Compound A)

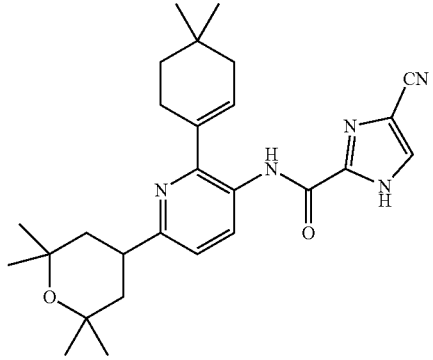

Compound A wherein the pharmaceutically acceptable salt is
Compound A, tosylate salt
characterized by an X-ray powder diffraction pattern comprising peaks at 5.1, 6.4 and 6.5 degrees two theta±0.2 degrees two theta.

2. The salt form of claim 1, wherein the X-ray powder diffraction pattern further comprises one or more of the following peaks: 5.8, 5.9, 16.3, 17.2, or 19.6 degrees two theta±0.2 degrees two theta.

3. A pharmaceutically acceptable salt form of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide (Compound A)

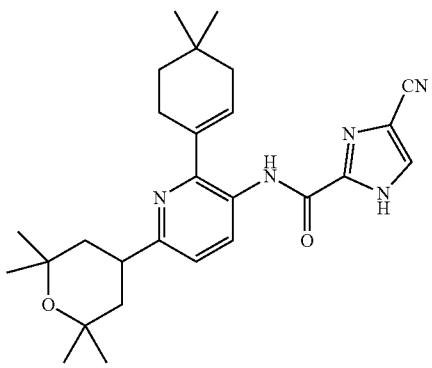

Compound A wherein the pharmaceutically acceptable salt is Compound A, tosylate salt characterized by an X-ray powder diffraction pattern substantially as depicted in FIG. 23.

4. A pharmaceutically acceptable salt form of 4-cyano-N-[2-(4,4-dimethylcyclohex-1-en-1-yl)-6-(2,2,6,6-tetramethyltetrahydro-2H-pyran-4-yl)pyridin-3-yl]-1H-imidazole-2-carboxamide (Compound A)

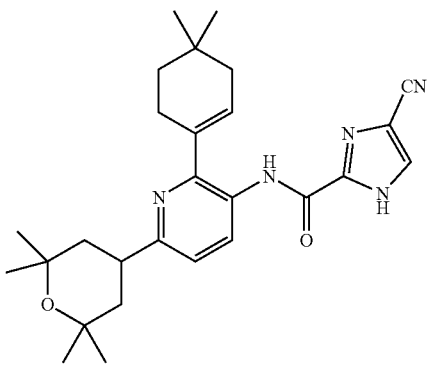

Compound A wherein the pharmaceutically acceptable salt is Compound A, tosylate salt characterized by a differential scanning calorimetry thermogram comprising endothermic events at about 155.9° C., about 207.4° C. and about 255.9° C.

5. A pharmaceutical composition comprising the salt form of claim 1 and at least one pharmaceutically acceptable excipient.

6. A pharmaceutical composition comprising the salt form of claim 3 and at least one pharmaceutically acceptable excipient.

7. A pharmaceutical composition comprising the salt form of claim 4 and at least one pharmaceutically acceptable excipient.

* * * * *